United States Patent
Kriesel et al.

(10) Patent No.: US 8,226,609 B2
(45) Date of Patent: *Jul. 24, 2012

(54) FLUID DISPENSER WITH ADDITIVE SUB-SYSTEM

(75) Inventors: Marshall S. Kriesel, St. Paul, MN (US); Joshua W. Kriesel, San Francisco, CA (US); Thomas N. Thompson, Richfield, MN (US)

(73) Assignee: BioQuiddity, Inc., San Francisco, CA (US)

( * ) Notice: Subject to any disclaimer, the term of this patent is extended or adjusted under 35 U.S.C. 154(b) by 21 days.

This patent is subject to a terminal disclaimer.

(21) Appl. No.: 12/455,617

(22) Filed: Jun. 3, 2009

(65) Prior Publication Data

US 2009/0275888 A1    Nov. 5, 2009

Related U.S. Application Data

(63) Continuation-in-part of application No. 11/823,084, filed on Jun. 25, 2007.

(51) Int. Cl.
*A61M 37/00* (2006.01)

(52) U.S. Cl. ..................................... 604/132

(58) Field of Classification Search .......... 604/131–151, 604/890.1, 891.1
See application file for complete search history.

(56) References Cited

U.S. PATENT DOCUMENTS

| | | | |
|---|---|---|---|
| 2,236,084 A | 3/1941 | Brown | |
| 4,140,117 A * | 2/1979 | Buckles et al. | 604/132 |
| 6,236,624 B1 | 5/2001 | Kriesel et al. | |
| 6,558,358 B2 * | 5/2003 | Rosoff et al. | 604/200 |
| 6,740,059 B2 * | 5/2004 | Flaherty | 604/67 |
| 7,220,245 B2 * | 5/2007 | Kriesel | 604/134 |

* cited by examiner

*Primary Examiner* — Matthew F Desanto
(74) *Attorney, Agent, or Firm* — James E. Brunton

(57) ABSTRACT

A compact fluid dispenser for use in controllably dispensing fluid medicaments, such as, antibiotics, analgesics, and like medicinal agents from the device reservoir which is provided in the form of a novel bellows-type assembly. The fluid dispenser includes a unique stored energy mechanism which takes the form of a constant force spring member of novel design that provides the force necessary to continuously and substantially uniformly expel fluid from the device reservoir. The device also includes novel adjustable flow rate control assembly that is disposed intermediate the fluid reservoir outlet and the outlet port of the device for precisely controlling the rate of fluid flow from the outlet port toward the patient.

14 Claims, 28 Drawing Sheets

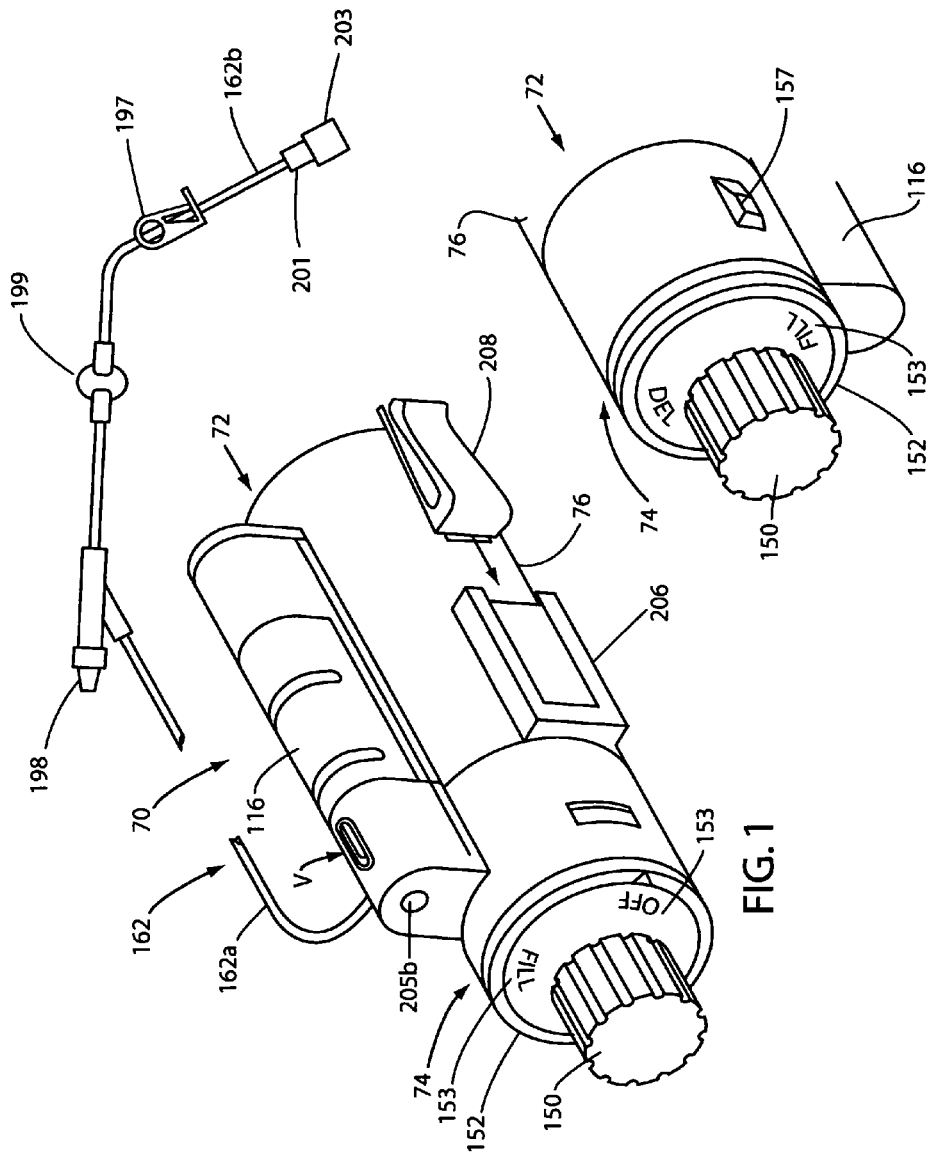

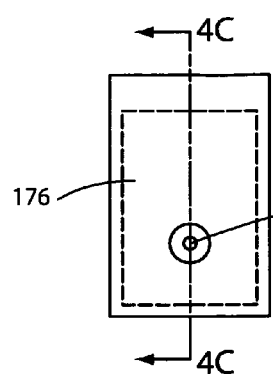
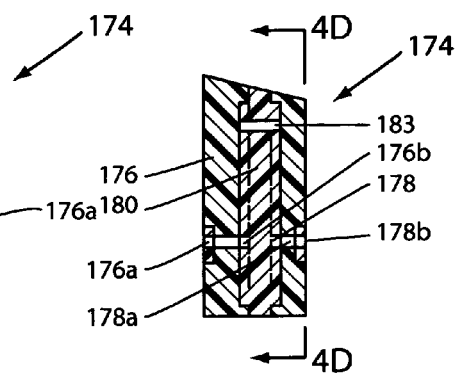
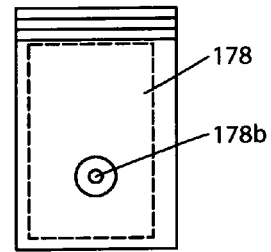
FIG. 4B            FIG. 4C            FIG. 4D
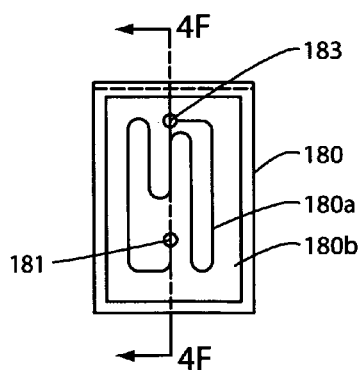
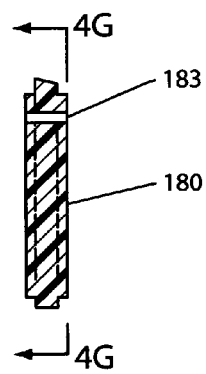
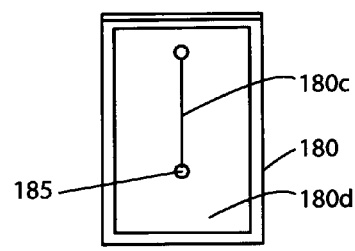
FIG. 4E            FIG. 4F            FIG. 4G

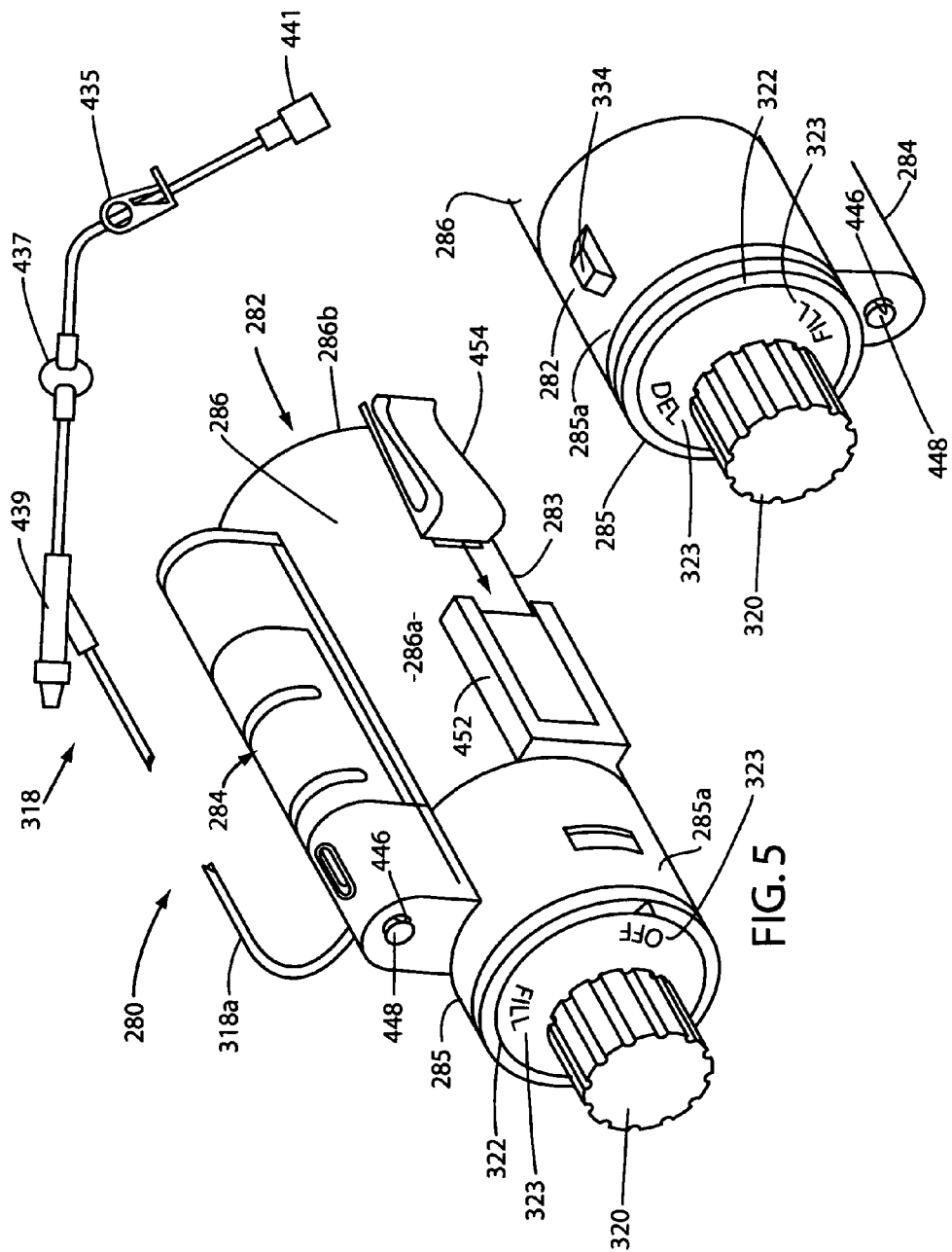

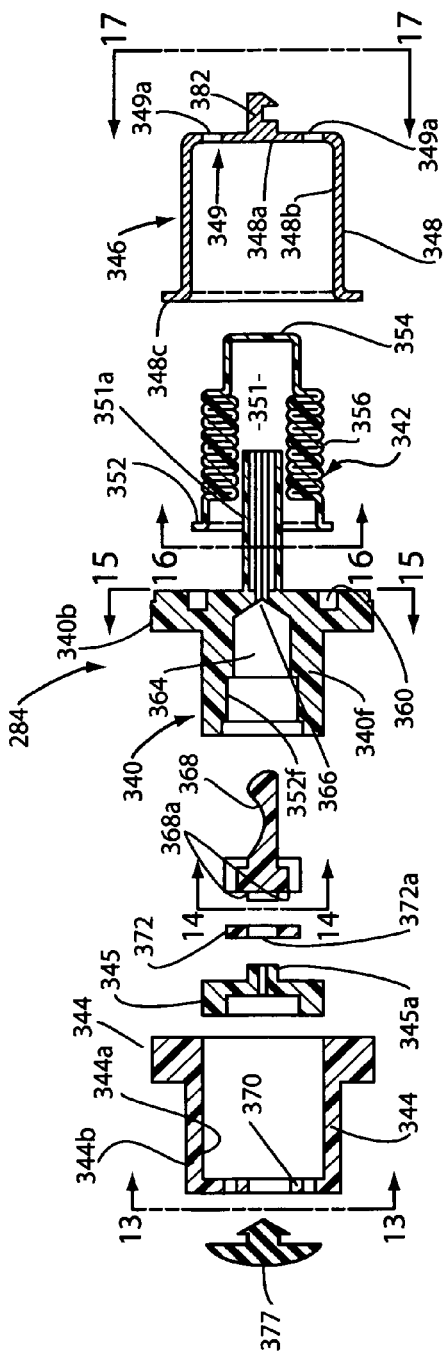
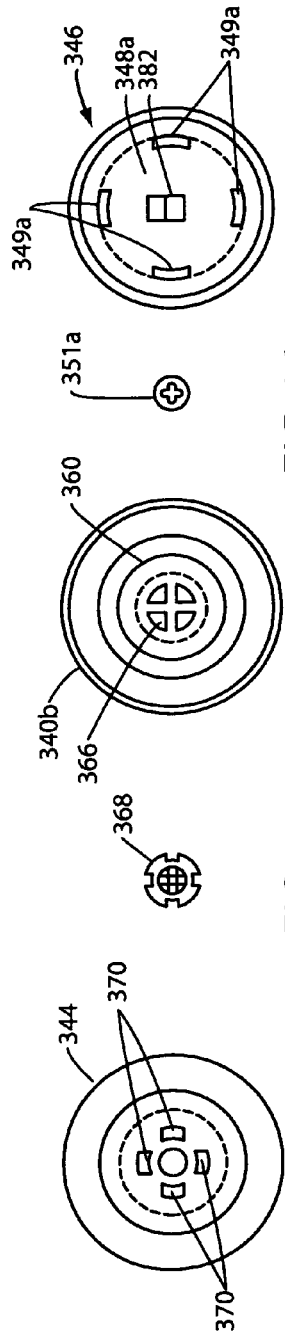

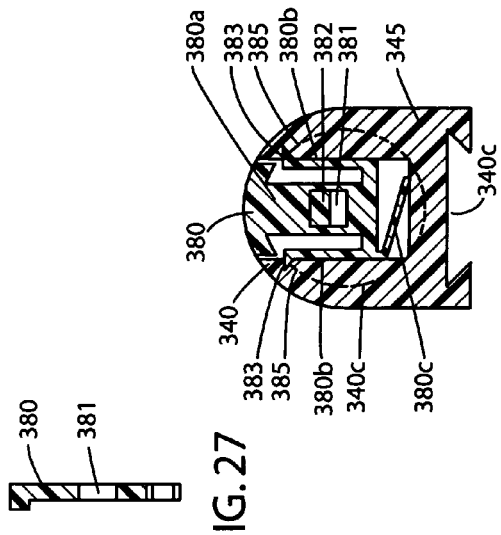
FIG. 26
FIG. 27
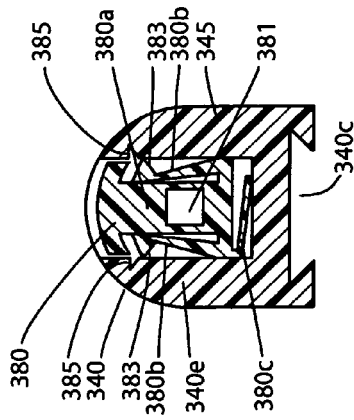
FIG. 29
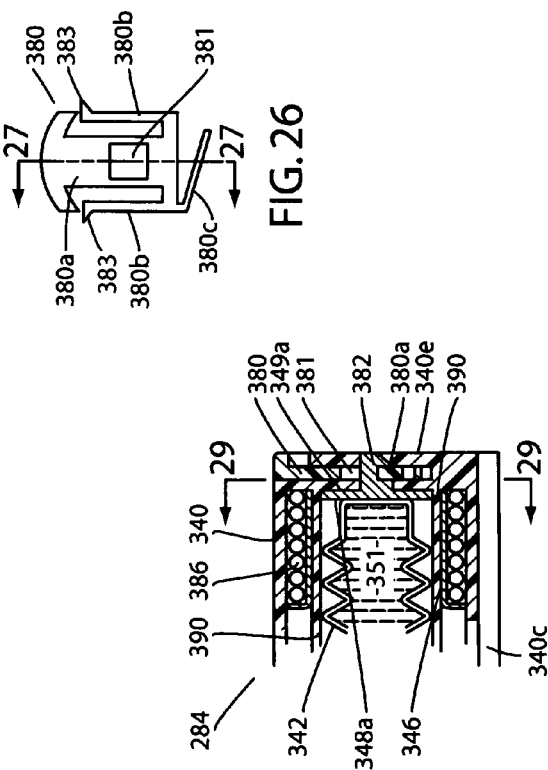
FIG. 28
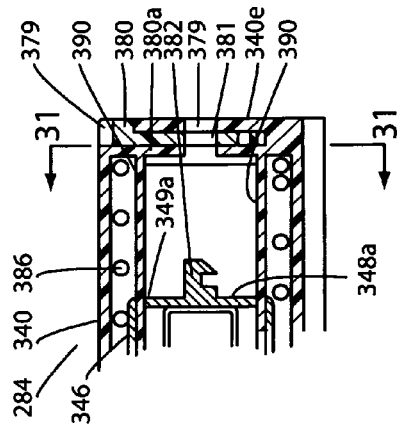
FIG. 31
FIG. 30

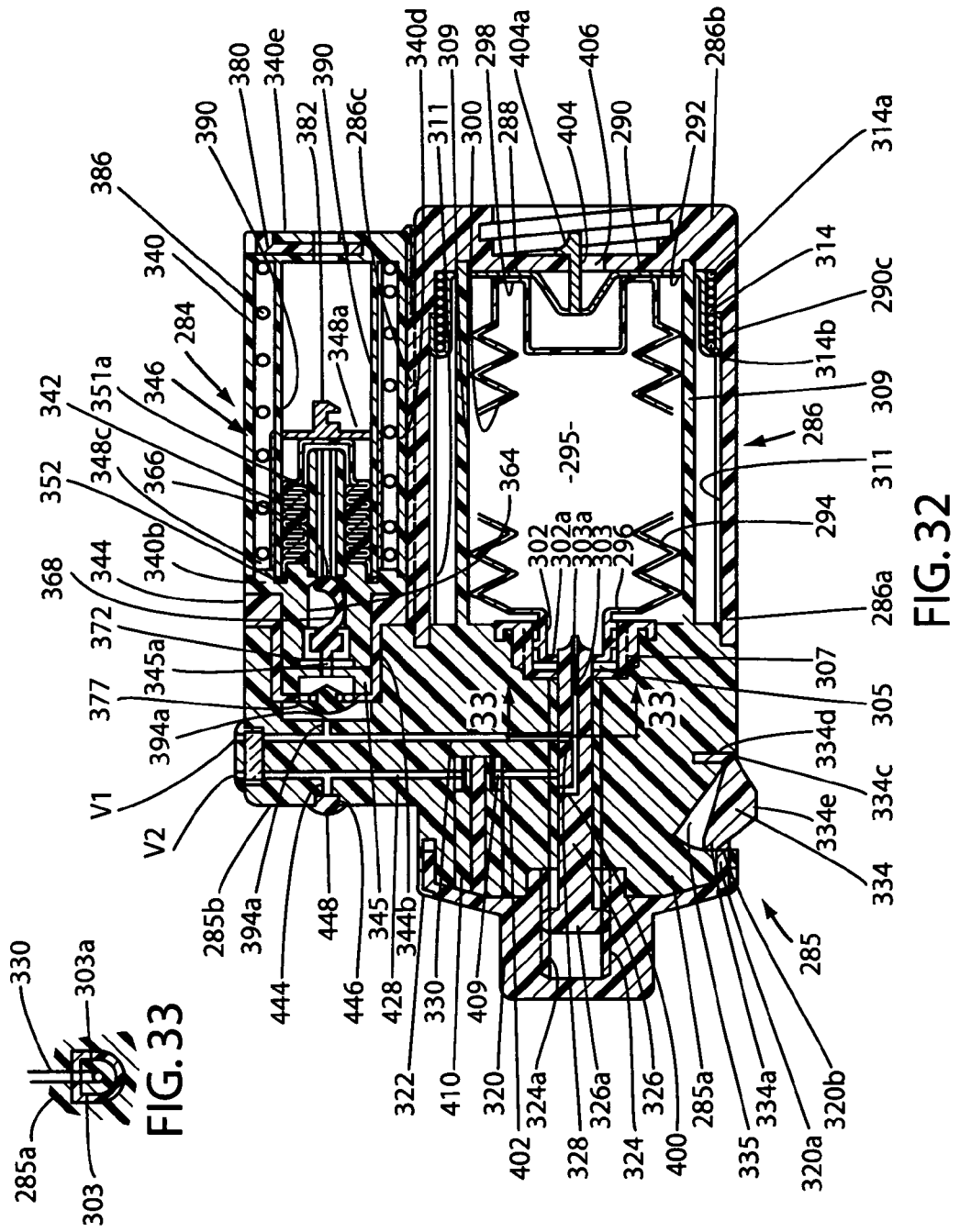

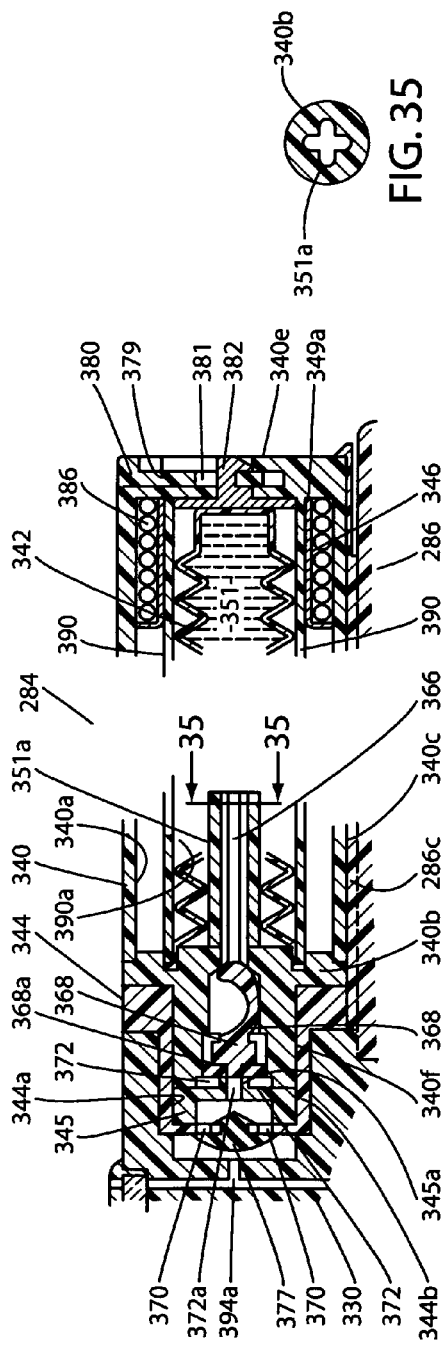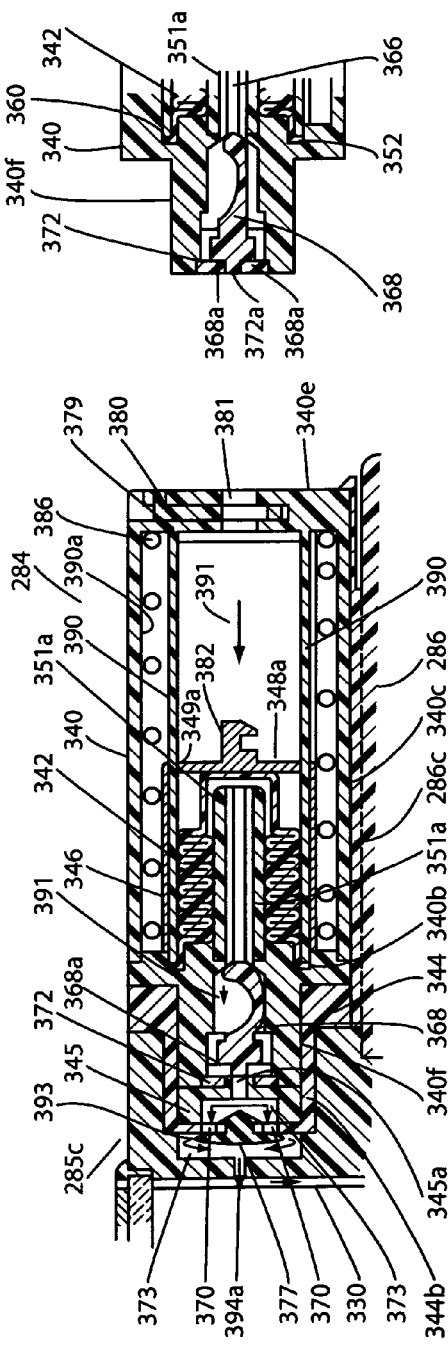

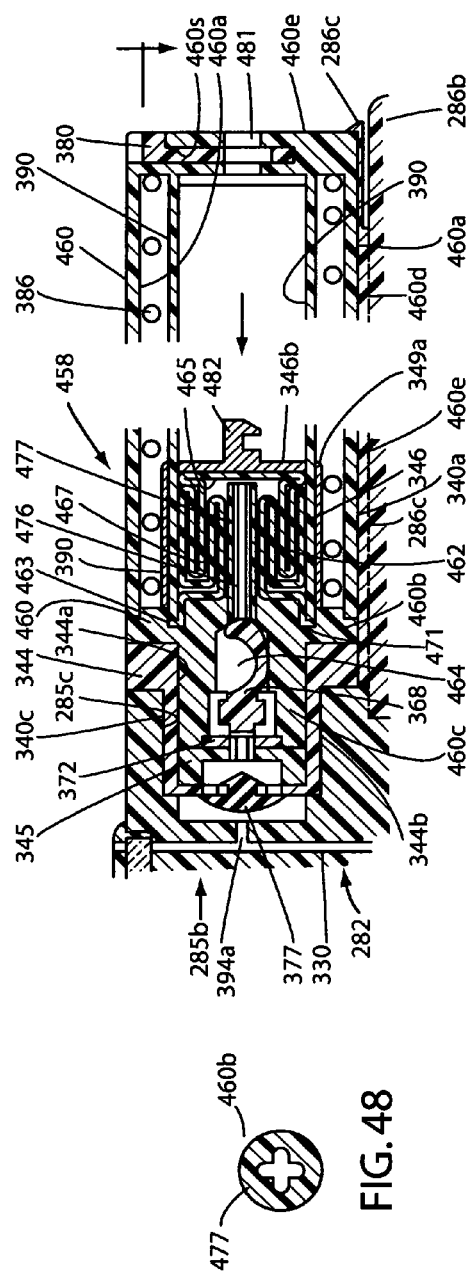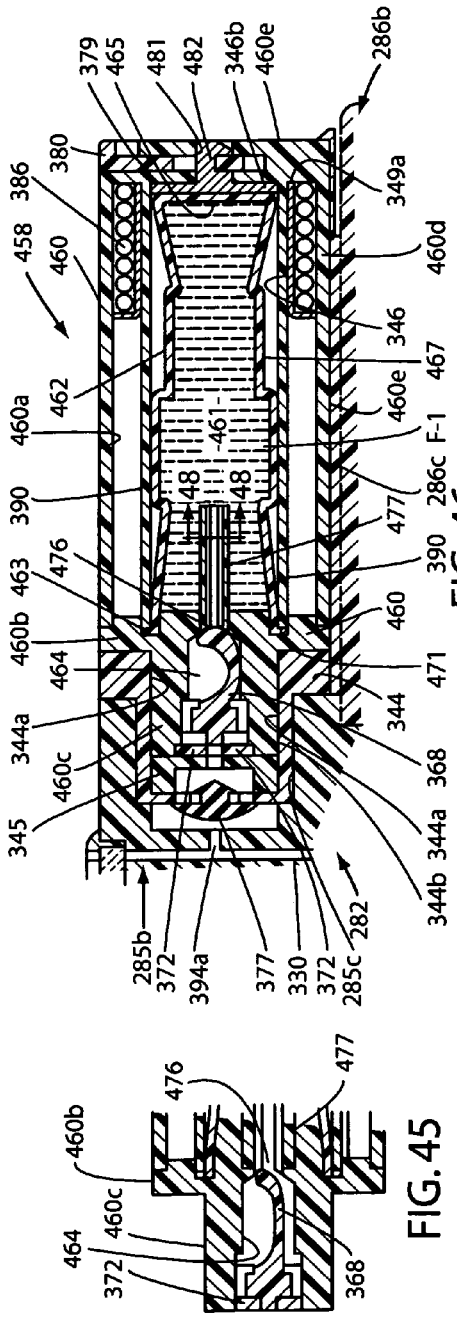

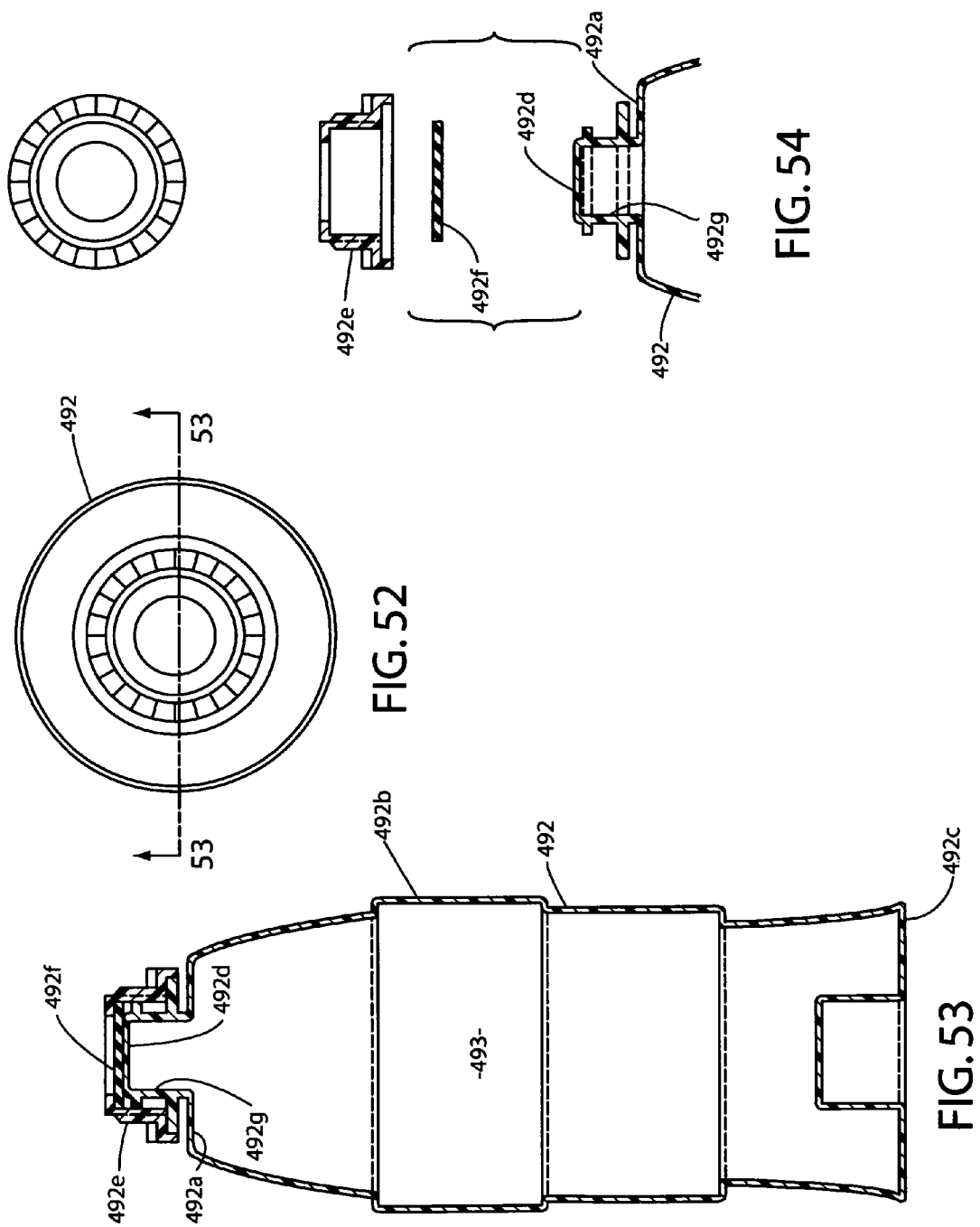

FLUID DISPENSER WITH ADDITIVE SUB-SYSTEM

CROSS-REFERENCE TO RELATED APPLICATIONS

This is a Continuation-in-Part of co-pending U.S. Ser. No. 11/823,084, filed Jun. 25, 2007.

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

The present invention relates generally to fluid dispensing devices. More particularly, the invention concerns medicament dispensers for dispensing medicinal fluids to ambulatory patients.

2. Description of Related Art Including Information Disclosed Under 37 CFR 1.97 and 1.98

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

The prior art gravity flow methods typically involve the use of intravenous administration sets and the familiar flexible solution bag suspended above the patient. Such gravimetric methods are cumbersome, imprecise and require bed confinement of the patient. Periodic monitoring of the apparatus by the nurse or doctor is required to detect malfunctions of the infusion apparatus. Accordingly, the prior art devices are not well suited for use in those instances where the patient must be transported to a remote facility for treatment.

As will be fully appreciated from the discussion that follows, the devices of the present invention are particularly useful in combat situations. The ability to quickly and efficaciously treat wounded soldiers, especially in unpredictable or remote care settings, can significantly improve chances for patient survival and recovery. Accurate intravenous (IV) drug and fluid delivery technologies for controlling pain, preventing infection, and providing a means for IV access for rapid infusions during patient transport are needed to treat almost all serious injuries.

It is imperative that battlefield medics begin administering life saving medications as soon as possible after a casualty occurs. The continuous maintenance of these treatments is vital until higher echelon medical facilities can be reached. A compact, portable and ready-to-use infusion device that could be easily brought into the battlefield would allow medics to begin drug infusions immediately. Additionally, it would free them to attend to other seriously wounded patients who may require more hands-on care in the trauma environment following triage. In most serious trauma situations on the battlefield, IV drug delivery is required to treat fluid resuscitation, as well as both pain and infection. Drug infusion devices currently available can impede the timely administration of IV infusions in remote care settings.

Expensive electronic infusion pumps are not a practical field solution because of their weight and cumbersome size. Moreover, today's procedures for starting IV infusions on the battlefield are often dangerous because the attending medic must complete several time consuming steps. The labor intensive nature of current gravity solution bag modalities can prevent medics from attending to other patients also suffering from life threatening injuries. In some cases, patients themselves have been forced to hold infusion bags elevated in order to receive the medication by gravity drip.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely, U.S. Pat. No. 5,743,879, discloses an injectable medicament dispenser for use in controllably dispensing fluid medicaments such as insulin, anti-infectives, analgesics, oncolytics, cardiac drugs, bio-pharmaceuticals and the like, from a pre-filled container at a uniform rate. The dispenser, which is quite dissimilar in construction and operation from that of the present invention, includes a stored energy source in the form of a compressively deformable, polymeric, elastomeric member that provides the force necessary to controllably discharge the medicament from a pre-filled container which is housed within the body of the device. After having been deformed, the polymeric, elastomeric member will return to its starting configuration in a highly predictable manner.

BRIEF SUMMARY OF THE INVENTION

By way of brief summary, one form of the dispensing device of the present invention for dispensing medicaments to a patient comprises a supporting structure; a carriage assembly interconnected with the supporting structure for movement between a first position and a second position; a semi-rigid collapsible reservoir carried by the carriage assembly; the collapsible reservoir having an outlet port; guide means connected to the supporting structure for guiding travel of the carriage assembly between the first position and said second positions; a stored energy source operably associated with the carriage assembly for moving the carriage assembly between the first and second position; adding means for adding medicaments to the fluid within the fluid reservoir and an administration set including an administration line interconnected with the outlet port of the reservoir.

Another form of the dispensing device of the invention for dispensing medicaments to a patient is similar to that described in the preceding paragraph, but the dispensing device comprises two major cooperating components, namely a dispenser unit and a separate, stand-alone additive sub-system.

With the forgoing in mind, it is an object of the present invention to provide a compact fluid dispenser for use in controllably dispensing fluid medicaments, such as, antibiotics, anesthetics, analgesics, and like medicinal agents from a pre-filled dispenser at a uniform rate.

Another object of the invention is to provide a small, compact fluid dispenser of simple construction that can be used in the field with a minimum amount of training.

Another object of the invention is to allow infusion therapy to be initiated quickly, at will, at point of care on the battlefield so that the attending medic or medical professional can more efficiently deal with triage situations in austere environments.

Another object of the invention is to provide a dispenser in which a stored energy source is provided in the form of a compressible, expandable or retractable member of novel construction that provides the force necessary to continuously and uniformly expel fluid from the device reservoir.

Another object of the invention is to provide a dispenser of the class described which includes a fluid flow control assembly that precisely controls the flow of the medicament solution to the patient.

Another object of the invention is to provide a dispenser that includes precise variable flow rate selection.

Another object of the invention is to provide a fluid dispenser of simple construction which includes a novel adding means for adding medicaments to the fluid contained within the fluid reservoir.

Another object of the invention is to provide a fluid dispenser as described in the preceding paragraph which embodies a semi-rigid collapsible container that includes a fluid reservoir that contains the beneficial agents to be delivered to the patient.

Another object of the invention is to provide a fluid dispenser of the class described which is compact and lightweight, is easy for ambulatory patients to use, is fully disposable and is extremely reliable in operation.

Another object of the invention is to provide a small, compact fluid dispenser that includes a housing to which vials can be connected for use in adding medicaments to the fluid within the fluid reservoir of the device.

Another object of the invention is to provide a fluid dispenser as described in the preceding paragraphs that is easy and inexpensive to manufacture in large quantities.

BRIEF DESCRIPTION OF SEVERAL VIEWS OF THE DRAWINGS

FIG. 1 is a generally perspective, top view of one form of the fluid dispensing device of the present invention for dispensing medicaments to a patient.

FIG. 2 is a fragmentary, generally perspective bottom view of the front portion of the fluid dispensing device shown in FIG. 1.

FIG. 4B is a front view of the rate control subassembly of the dispenser portion of the device.

FIG. 4C is a cross-sectional view taken along lines 4C-4C of FIG. 4B.

FIG. 4D is a view taken along lines 4D-4D of FIG. 4C.

FIG. 4E is a front view of the rate control plate of the rate control subassembly shown in FIG. 4C of the drawings.

FIG. 4F is a cross-sectional view taken along lines 4F-4F of FIG. 4E.

FIG. 4G is a view taken along lines 4G-4G of FIG. 4F.

FIG. 5 is a generally perspective, top view of an alternate form of the fluid dispensing device of the present invention for dispensing medicaments to a patient.

FIG. 6 is a fragmentary, generally perspective, bottom view of the front portion of the fluid dispensing device shown in FIG. 5.

FIG. 12 is a longitudinal, cross-sectional, exploded view of the additive sub-system of the fluid delivery dispenser illustrated in FIG. 9.

FIG. 13 is a cross-sectional view taken along lines 13-13 of FIG. 12.

FIG. 14 is a cross-sectional view taken along lines 14-14 of FIG. 12.

FIG. 15 is a cross-sectional view taken along lines 15-15 of FIG. 12.

FIG. 16 is a cross-sectional view taken along lines 16-16 of FIG. 12.

FIG. 17 is a cross-sectional view taken along lines 17-17 of FIG. 12.

FIG. 26 is a front view of the carriage locking and release member of the additive sub-system.

FIG. 27 is a cross-sectional view taken along lines 27-27 of FIG. 26.

FIG. 28 is a fragmentary, cross-sectional view of one end of the additive sub-system of the invention illustrating the carriage locking and release member in a carriage locking position.

FIG. 29 is a cross-sectional view taken along lines 29-29 of FIG. 28.

FIG. 30 is a cross-sectional view, similar to FIG. 28, but showing the carriage locking and release member in a carriage release position.

FIG. 31 is a cross-sectional view taken along lines 31-31 of FIG. 30.

FIG. 32 is a longitudinal, cross-sectional view, similar to FIG. 7, but showing the configuration of the dispenser following filling of the fluid reservoir.

FIG. 33 is a cross-sectional view taken along lines 33-33 of FIG. 32.

FIG. 34 is a cross-sectional view of the additive sub-system of the invention further illustrating the carriage locking and release member in a carriage locking position and showing the fill-vial in a filled condition.

FIG. 35 is a cross-sectional view taken along lines 35-35 of FIG. 34.

FIG. 36 is a fragmentary, cross-sectional view of the forward end of the additive sub-system of the invention illustrating the main check valve in a sealing configuration.

FIG. 37 is a cross-sectional view similar to FIG. 34, but showing the carriage locking and release member in a carriage release position and showing the fill-vial as it appears following filling of the reservoir of the dispenser portion of the device.

FIG. 45 is a fragmentary, cross-sectional view of the forward end of an alternate form of the additive sub-system of the invention illustrating the main check valve in a sealing configuration.

FIG. 46 is a longitudinal, cross-sectional view of the alternate form of additive sub-system shown interconnected with the upper portion of the dispenser unit.

FIG. 47 is a longitudinal, cross-sectional view of the alternate form of additive sub-system, similar to FIG. 46, but showing the carriage locking and release member in a carriage release position and showing the fill-vial as it appears following filling of the reservoir of the dispenser unit portion of the device.

FIG. 48 is an enlarged cross-sectional view taken along lines 48-48 of FIG. 46.

FIG. 52 is a top view of the reservoir housing of the fluid dispenser portion of the device shown in FIG. 51.

FIG. 53 is a cross-sectional view taken along lines 53-53 of FIG. 52.

FIG. 54 is an exploded, cross-sectional view of the upper neck portion of the reservoir housing of the fluid dispenser portion of the device shown in FIG. 53.

DETAILED DESCRIPTION OF THE INVENTION

Figure 3:
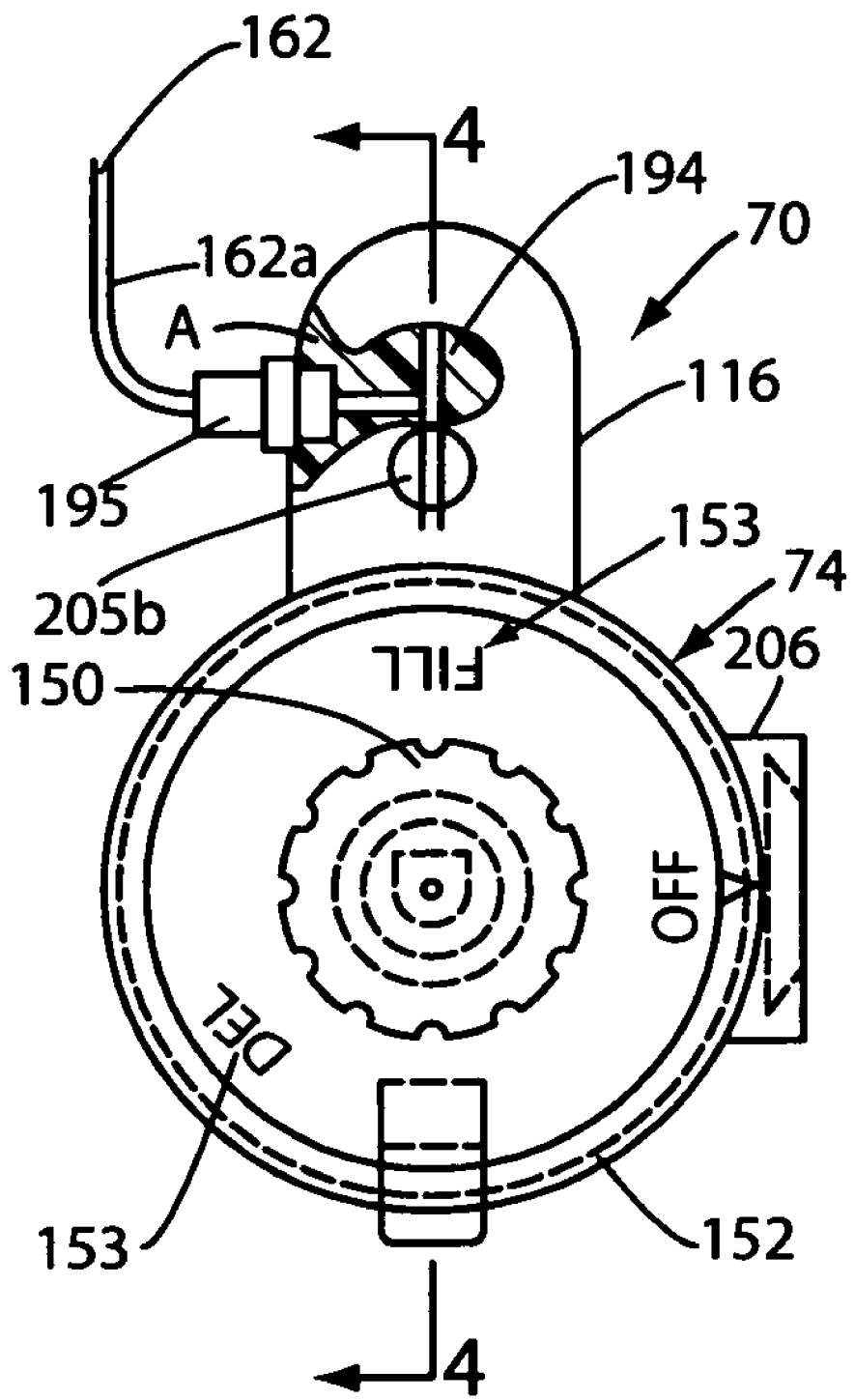
FIG. 3 is an enlarged front view of the fluid dispensing device shown in FIG. 1.

Referring to the drawings and particularly to FIGS. 1 through 4, one form of the dispensing device of the present invention for dispensing medicaments to a patient is there shown and generally designated by the numeral 70. The dispensing device here includes a housing 72 which includes a control portion 74 and a generally cylindrically shaped reservoir housing 76 that is interconnected with the control portion 74 in the manner best seen in FIG. 4 of the drawings. Housing 72 can be constructed from metal, plastic or any suitable material. Reservoir housing 76 includes a generally cylindrically shaped wall portion 76a and a base portion 76b.

Figure 4:
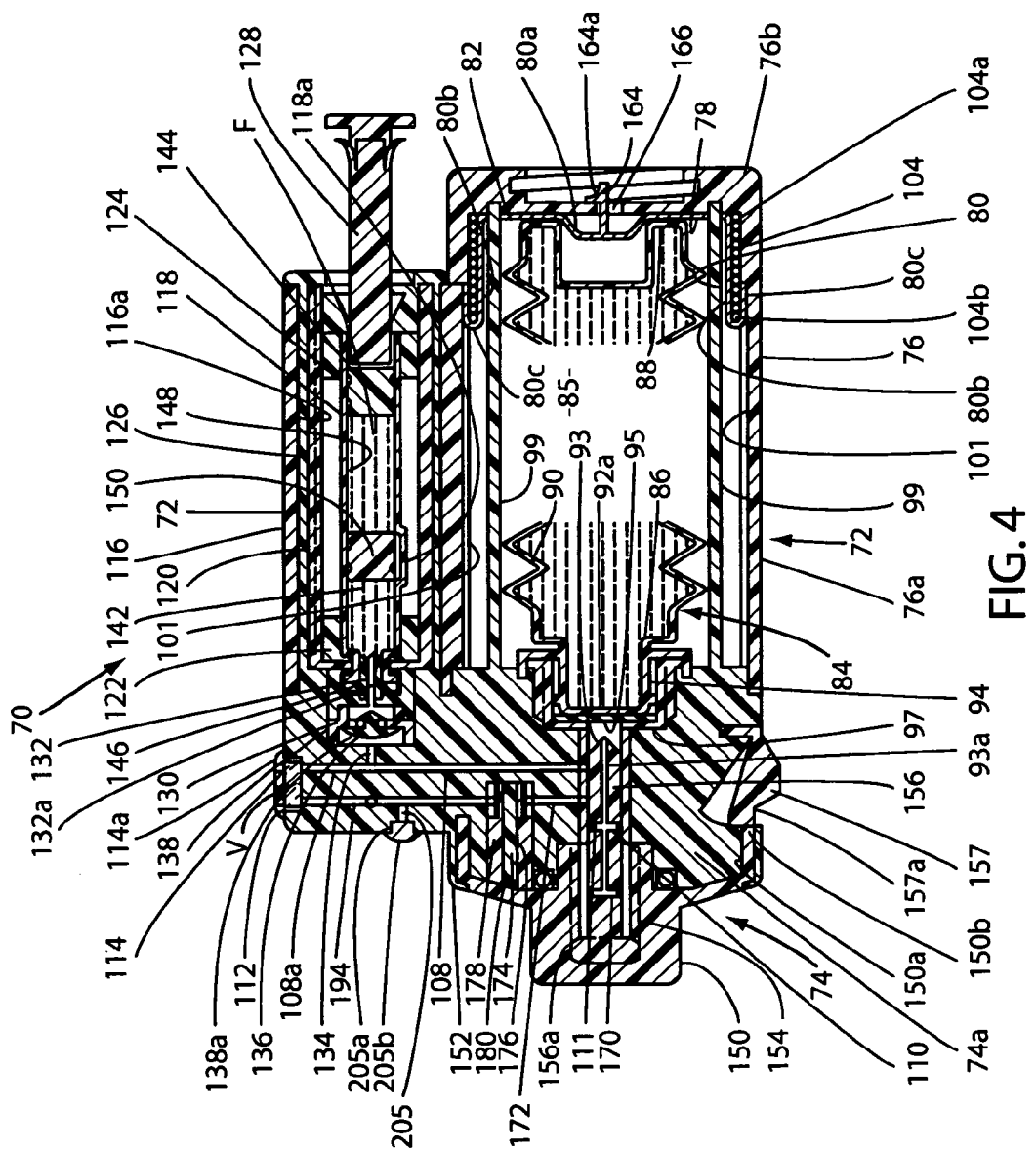
FIG. 4 is a cross-sectional view taken along lines 4-4 of FIG. 3.
Figure 4A:
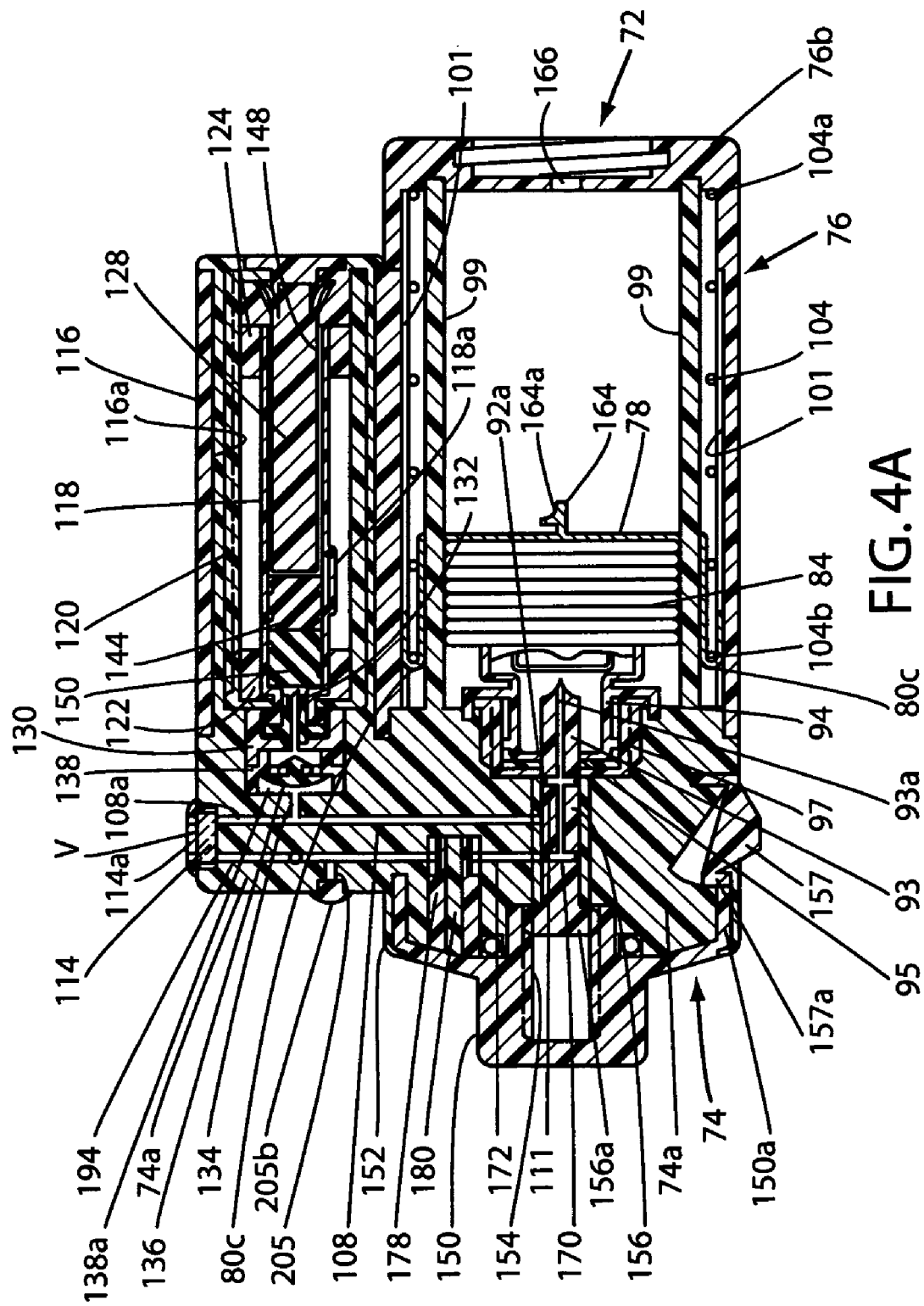
FIG. 4A is a cross-sectional view similar to FIG. 4, but showing the device following the collapse of the reservoir housing.

Disposed within wall portion 76a is a carriage assembly 78 which is movable between a first position shown in FIG. 4 and a second position shown in FIG. 4A. As best seen by referring to FIG. 4, carriage assembly 78 comprises a carriage 80 having a carriage base 80a that is provided with a plurality of circumferentially spaced openings 82 and a generally cylindrically shaped sidewall 80b which terminates in circumferentially spaced, radially outwardly extending flanges 80c. Carriage assembly 78 is releasably locked in its first position by a novel locking means the character of which will presently be described.

Carried by carriage assembly 78 is a semi-rigid reservoir defining assembly 84 that defines a fluid reservoir 85. As indicated in FIG. 4, reservoir defining assembly 84 comprises a top wall 86, a bottom wall 88 and an accordion-like side wall 90. Connected to top wall 86 is a neck portion 94 that is sealed by a closure wall 92a.

In the preferred form of the invention reservoir defining assembly 84 is formed in accordance with an aseptic blow-fill seal manufacturing technique which is of a character well understood by those skilled in the art. This technique involves the continuous plastic extrusion through an extruder head of a length of parison in the form of a hollow tube between and through two co-acting first or main mold halves. The technique further includes the step of cutting off the parison below the extruder head and above the main mold halves to create an opening which allows a blowing and filling nozzle assembly to be moved downwardly into the opening in the parison for molding the molded container. Further details concerning the technique are available from Rommelag GMBH of Stutgart, Germany and Weiler Engineering of Elgin, Ill.

In a manner presently to be described, a collapsible container is accessible via a penetrating member 93 that is adapted to pierce closure wall 92a as well as a pierceable membrane 95 which is positioned over closure wall 92a by means of a closure cap 97 which is affixed to the neck portion 94 of container assembly 84 (FIG. 4). As previously described, the basic container 84 is formed using the earlier described aseptic blow-fill technique and the reservoir portion of the container is sealed by the thin closure wall 92a. The piercable membrane 95 is then positioned over the closure wall and the closure cap 97 is positioned over the piercable septal membrane and secured to neck portion 94 by any suitable means such as adhesive bonding, sonic or heat welding.

An important feature of the invention resides in the provision of novel guide means for guiding travel of carriage assembly 78 between the first position shown in FIG. 4 and a second position. In the present form of the invention this important guide means comprises a plurality of circumferentially spaced guide members 99 which are connected to and extend outwardly from body 74a of control portion 74 (FIG. 4). As indicated in the drawings, guide members 99 are slidably received within openings 82 provided in carriage base 80a (FIG. 4) so that, as the carriage assembly travels from its first position toward its second position, guide members 99 precisely guide its travel. Also forming a part of the guide means of the apparatus of the present invention are a plurality of circumferentially spaced guide grooves 101 that are formed on the inner wall of outer housing 76 (FIG. 4).

To controllably move the carriage assembly from its first position to its second position, novel stored energy means are provided. This novel stored energy means, which is operably associated with carriage assembly 78, is here provided in the form of a coiled spring 104. As illustrated in FIG. 4, one end 104a of the coil spring 104 is disposed in engagement with the threaded base portion 76b of reservoir housing 76 and the other end 104b thereof is disposed in engagement with radially outwardly extending flange segments 80c of carriage 80. With this construction, following penetration of the reservoir septum, and when the locking means of the invention is manipulated in a manner to unlock the carriage assembly from base portion 76b of the outer housing, spring 104 will move from its retracted position shown in FIG. 4 to its expanded position shown in FIG. 4A, and in so doing will controllably move the carriage assembly from its starting position shown in FIG. 4 to its fully deployed or extended position and in so doing will controllably move the carriage assembly from its starting position shown in FIG. 4 to its fully deployed or extended position. As will be described more fully in the paragraphs that follow, as the carriage assembly moves toward its deployed position, the accordion-like side wall 90 of the reservoir defining container will move into the collapsed configuration and in so doing will cause the medicinal fluid contained within the container to be controllably expelled therefrom.

Forming an important aspect of the apparatus of the present invention is adding means carried by portion 76 of housing 72 for adding injectable medicaments to the fluid within the fluid reservoir 85. The details of construction and operation of this important adding means will presently be discussed. As best seen in FIG. 4, body 74a of control portion 74 includes a fluid passageway 108 that is in communication with the fluid passageway of penetrating member 93 via passageways 110 and 111. Proximate its outer extremity 108a, fluid passageway 108 communicates with a cavity 112 formed within control portion 74 (See FIG. 4). Disposed within cavity 112 is a porous filter 114 which comprises a part of the vent means "V" of this latest form of the invention for venting to atmosphere any gasses that would otherwise be trapped within the fluid passageways of the device during the medicament adding step. Filter 114, which is of a conventional construction such as hydrophobic-treated, sintered metal or porous membrane, is held in position by a retainer 114a.

Control portion 74 of housing 72 also includes a vial housing 116 having a chamber 116a for telescopically receiving a medicament containing reconstitution-type fill-vial 118. An elongated vial 120, which is disposed within chamber 116a, along with first and second spacers 122 and 124, function to hold vial 118 in a proper position within chamber 116a. Vial 120 is telescopically receivable within a vial tube 126, which in turn carries a pusher member 128, the purpose of which will presently be described. Also carried by control portion 74 in close proximity with vial 120 is a needle holding component 130. As shown in FIG. 4, needle holding component 130 carries a longitudinally extending, elongated hollow needle 132 having a flow passageway 132a that communicates with fluid passageway 108 via a stub passageway 134 and a conventional check valve 136 which is carried by a check valve housing 138. Vial 118, vial 120, vial tube 126, needle holding component 130 and hollow needle 132 together comprise one form of the adding means of the device of the present invention. The method of operation of this important adding means will presently be described.

Referring particularly to FIG. 4, the medicament containing fill-vial 118 comprises a container of special design that uniquely contains a lyophilized drug 142. Vial 118 is sealed at one end by a slidable elastomeric plunger 144 and at the other end by a pierceable septum 146. Formed intermediate the ends of the vial is a raised outer wall by-pass portion 118a, which permits the fluid "F" that is contained within a chamber 148 to bypass a barrier stopper 150 as the barrier stopper is urged inwardly of the container by pressure exerted thereon by the fluid, which is being pushed by plunger 144 resulting from force exerted on pusher element member 128 (see FIG. 4).

A continued inward pressure exerted on plunger 144 will cause fluid "F" to flow past barrier member 150 via the internal passageway defined wall portion 118a so as to reconstitute the lyophilized drug 142. A continued pressure exerted on plunger 144 by the pusher member will cause the reconstituted drug formed by the fluid "F" which has been intermixed with drug to flow through hollow needle 132, into a chamber 138a formed in check valve housing 138, past check valve 136, into a stub passageway 134, then into passageway 108 and finally into the device reservoir 85.

Device reservoir 85 and reconstitution medicament containing fill-vial 118 can be of various volumes ranging from about 5 ml to about 50 ml.

To control the flow of medicinal fluid from the adding means into the reservoir 85 and then, during the fluid dispensing step, out of reservoir 85 toward the administration set 162 of the invention, novel flow control means are provided. This novel fluid flow control means, which is housed within the control portion 74 of the device, here comprises two cooperating components, namely a rate control means for controlling the rate of fluid flow from the semi-rigid collapsible reservoir toward the administration set and an operating means for controlling fluid flow from the adding means into the reservoir 85 and then, after the reservoir has been filled, out of reservoir 85 toward the rate control means.

Considering first the operating means of the invention, this important means, which first controls fluid flow from the adding means toward the reservoir 85 and subsequently controls fluid flow between collapsible reservoir 85 and the rate control means, here comprises a control knob 150 that is rotatably mounted on body 74a of control portion 74. As best seen in FIG. 4, control knob 150 is held in position on body 74a by a knob retaining ring 152. Control knob 150, which is provided with control indicia 153 (FIG. 3), has an axial bore 154 having threads that threadably receive the head portion 156a of an elongated needle housing 156 that carries penetrating member 93 (FIGS. 4 and 4A). With this construction, an initial rotation of knob 150 will cause the needle housing 156 to controllably move from the position shown in FIG. 4 to the fill position, wherein fluid passageway 111 aligns with fill passageway 108 formed in control body portion 74a. This initial rotation of control knob 150 will also cause penetrating member 93 to pierce both septal membrane 95 as well as closure wall 92a of the reservoir container. This movement of the housing 156 and the penetrating member 93 opens fluid communication between the fill-vial 118 and the fluid reservoir 85 via penetrating needle 93, the opened check valve 136, stub passageway 134, fill passageway 108, stub passageway 111, and the internal fluid flow passageway of penetrating member 93. In the manner previously discussed, an inward force exerted on pusher member 128 will cause the fluid "F" to flow past barrier member 150 via the internal by-pass passageway defined by wall portion 118a so as to reconstitute the lyophilized drug 142. A continued pressure exerted on plunger 144 by the pusher member will cause the reconstituted drug formed by the fluid "F", which has been intermixed with the drug, to flow through penetrating needle 132 and then on to the fluid reservoir 85. After the reservoir is filled, check valve 136 will return to its initial closed position shown in FIG. 4 blocking reverse fluid flow from collapsible reservoir 85 toward fill-vial 118.

To prevent accidental rotation of control knob 150, the operating means further includes indexing means, here provided in the form of an indexing button 157. This important indexing means functions to prevent rotation of the control knob until the indexing button, which is pivotally mounted on the side of the control portion of the device (FIG. 4), is pivoted inwardly. The skirt portion 150a of the control knob is provided with a plurality of circumferentially spaced notches 150b that closely receive a locking tab 157a formed on indexing button 157 when the button is biased toward its outward locking position. To accomplish the initial rotational step, described in the preceding paragraph, the indexing button 157 is pushed inwardly to move the locking tab 157a out of engagement with the notch within which it resides and the control knob is rotated from the "OFF" position (FIG. 3) to the "FILL" position. Release of the indexing button will then cause the outwardly biased locking tab 157a to move into engagement with an appropriate locking notch so as to lock the control knob in the "FILL" position.

After the diluent reservoir-filling step has been completed in the manner previously described, the fluid contained within the field reservoir can be dispensed to the patient by once again pivoting the indexing button 157 inwardly to move the locking tab 157a out of engagement with the notch within which it resides. This done, the control knob can be further rotated to the "DEL." position thereby causing the needle housing 156 to controllably move from the position shown in FIG. 4 to the fluid delivery position shown in FIG. 4A. In this position fluid passageway 170 aligns with dispensing passageway 172 formed in control body portion 74a so that fluid can flow from reservoir 85 toward the administration set 162 via the flow rate control means of the invention the character of which will presently be described.

To cause the fluid to flow from reservoir 85 toward the flow rate control means, the locking means of the invention must be manipulated in a manner to release the carriage assembly from base wall 76b of reservoir housing 76. In this regard, as best seen in FIG. 4, the carriage locking means includes a locking member 164 having a yieldably deformable locking tab 164a which extends through a strategically shaped opening 166 provided in the base wall 76b of reservoir housing 76. With this construction, an inward force exerted on the locking member will deform the locking tab 164 in a manner to permit it to pass through the opening 166 and in so doing release the carriage from the base wall 76b. Release of the carriage will permit the stored energy means, or coiled spring 104, to move the carriage from a position shown in FIG. 4 into the extended position. As the semi-rigid, accordion-like side wall of the container collapses due to the urging of the coiled spring, the medicinal fluid contained within the container will be controllably expelled therefrom and will flow toward the fluid passageway of penetrating member 93 which has now moved into a downward position. From the fluid passageway of penetrating member 93, fluid will flow into a stub passageway 170 formed in needle housing 156. With the penetrating member in its downward position, stub passageway 170 is aligned with a passageway 172 which forms the inlet to the fluid rate control means of the invention.

Referring to FIGS. 4A through 4G, the important fluid rate control means of the invention comprises a rate control housing 174, which includes a front cover 176 having an inlet 176a and an outlet 176b. Rate control housing 174 also includes a back cover 178 having an inlet 178a and an outlet 178b. Disposed between the front and back cover is a novel rate control plate 180 having a uniquely configured, circuitous fluid flow channel 180a formed on the first surface 180b thereof and a substantially linear fluid flow channel 180c formed on the second surface 180d thereof.

With the construction described in the preceding paragraphs, as the accordion-like side wall of the fluid container collapses in a controlled manner, fluid will flow from reservoir 85 into the flow passageway of penetrating member 93, into stub passageway 170 and then into the inlet passageway 176a of the rate control means. From passageway 172, the fluid will flow into the inlet 176a of front cover 176 and then into inlet 181 of rate control plate 180. The fluid will then flow through the circuitous fluid flow channel and into the inlet of the linear fluid flow channel. Next, the fluid will flow through outlet 185 into inlet 178a of back cover 178, outwardly through outlet 178b thereof and then into an elongated passageway 194 formed in body 74a of control portion 74. From the elongated channel 194 the fluid will flow onward to the administration set 162 and then to the patient. It is apparent that by varying the geometry, including the length, width and depth of the flow control channel 180a, the rate of fluid flow to the administration set and to the patient can be readily varied.

As best seen in FIG. 3, administration set 162 is sealably connected to the control portion 74 by a connector 195 so that the proximal end 162a of administration line 162 of the administration set is in communication with an outlet fluid passageway 194. Disposed between the proximal end 162a and the distal end 162b of the administration line are a conventional clamp 197, a conventional gas vent and a conventional filter 199 and an injector site 198. Provided at the distal end 162b of the administration line is a luer connector 201 and luer cap 203 of conventional construction (See FIG. 1).

To accomplish residual drug recovery from reservoir 85 as may be required, recovery means are provided. In this regard, as best seen in FIG. 4, a stub passageway 205 formed in body 74a also communicates with fluid passageway 194. Stub passageway 205 also communicates with a cavity 205a formed in body 74a. Sealably mounted within cavity 205a is a non-coring pierceable septum 205b (FIG. 4) which is pierceable by the needle of a conventional syringe that can be used to accomplish residual drug recovery from reservoir 85.

As illustrated in FIG. 1, housing 76 is provided with a belt clip receiving member 206 to which a belt clip 208 can be slidably interconnected. When the belt clip 208 is connected with receiving member 206 the device can be conveniently carried on the user's belt during the medicament dispensing step.

Figure 7:
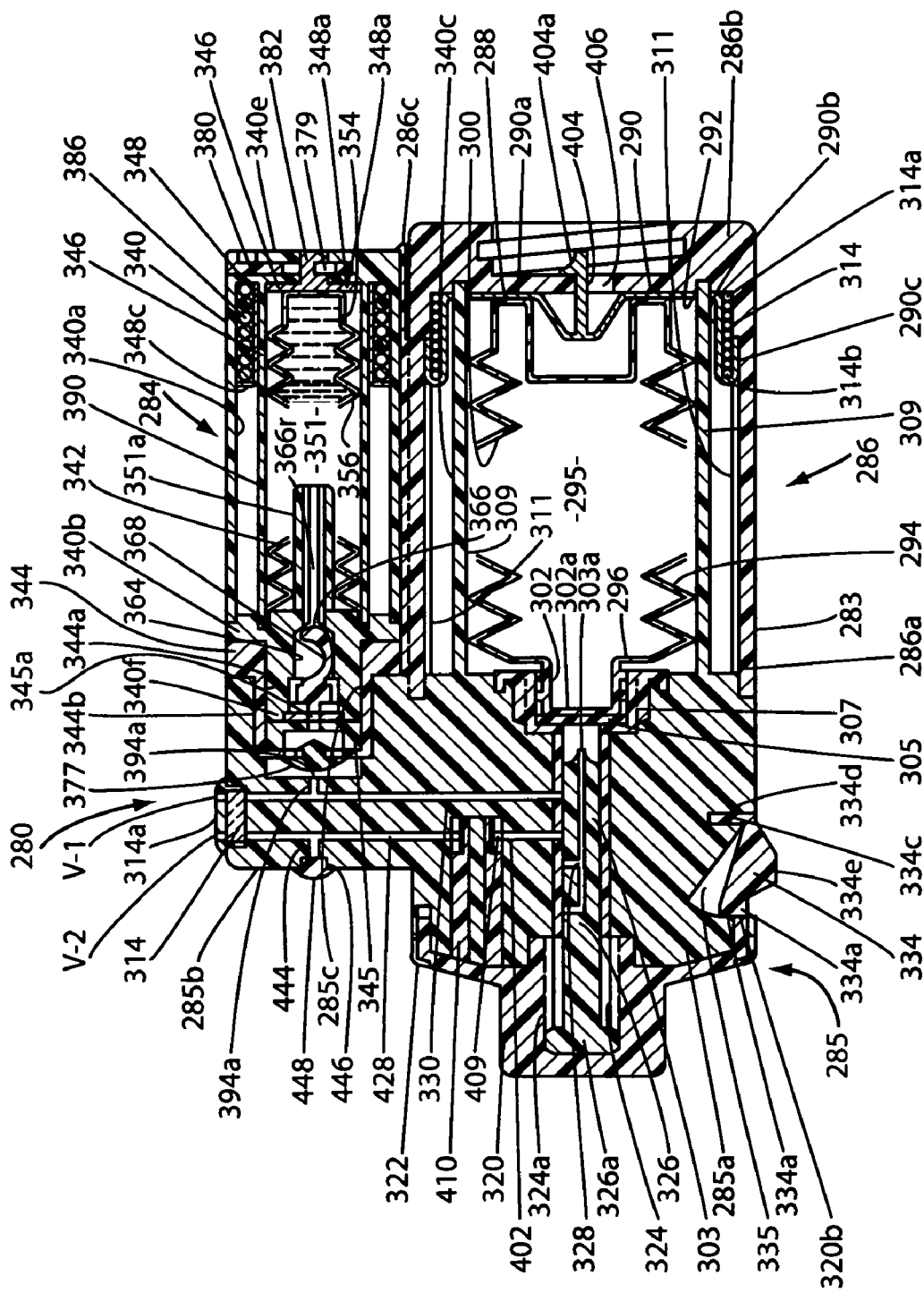
FIG. 7 is longitudinal, cross-sectional view of the fluid dispensing device shown in FIG. 5.
Figure 8:
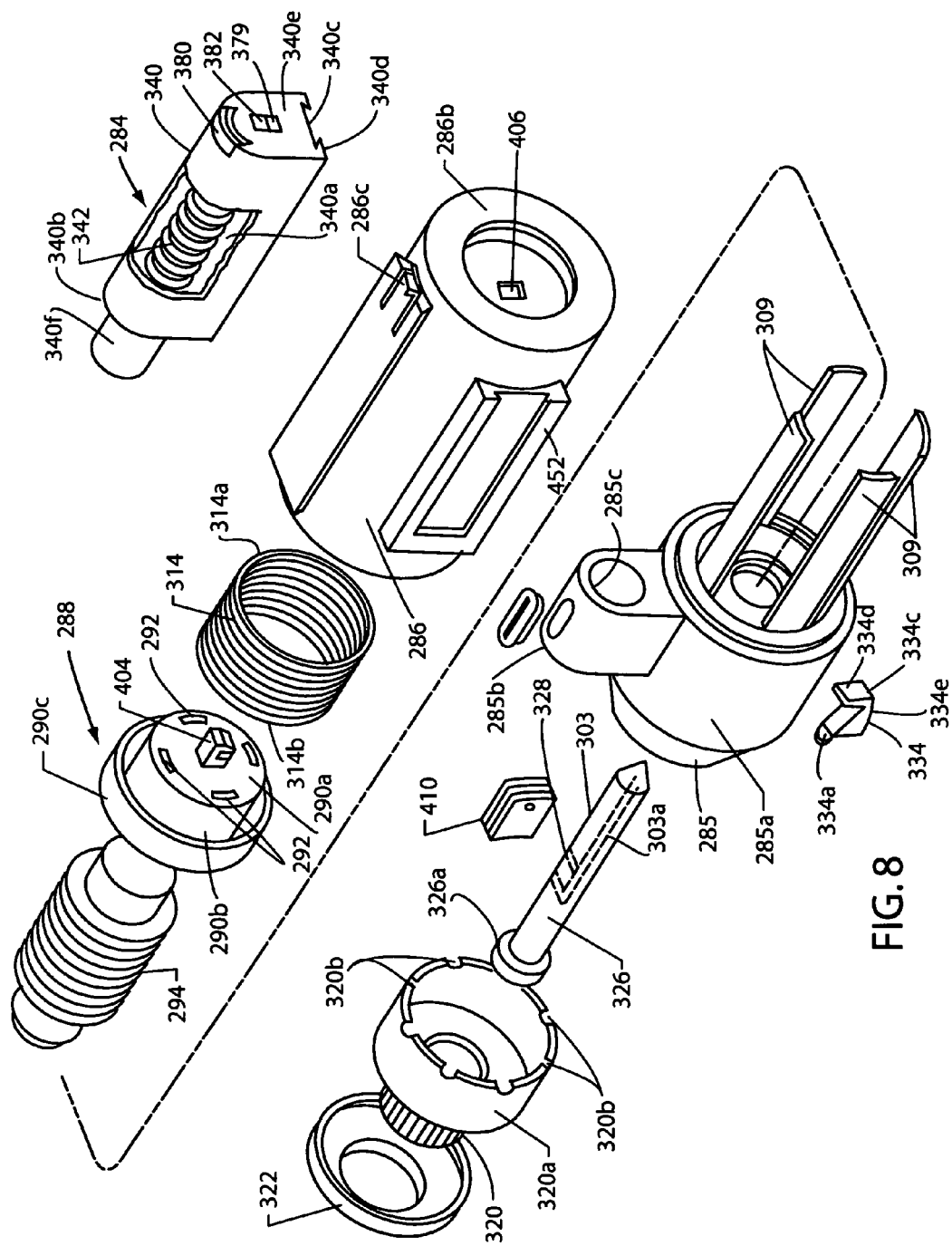
FIG. 8 is a generally perspective, exploded view of the fluid dispensing device illustrated in FIG. 7.
Figure 9:
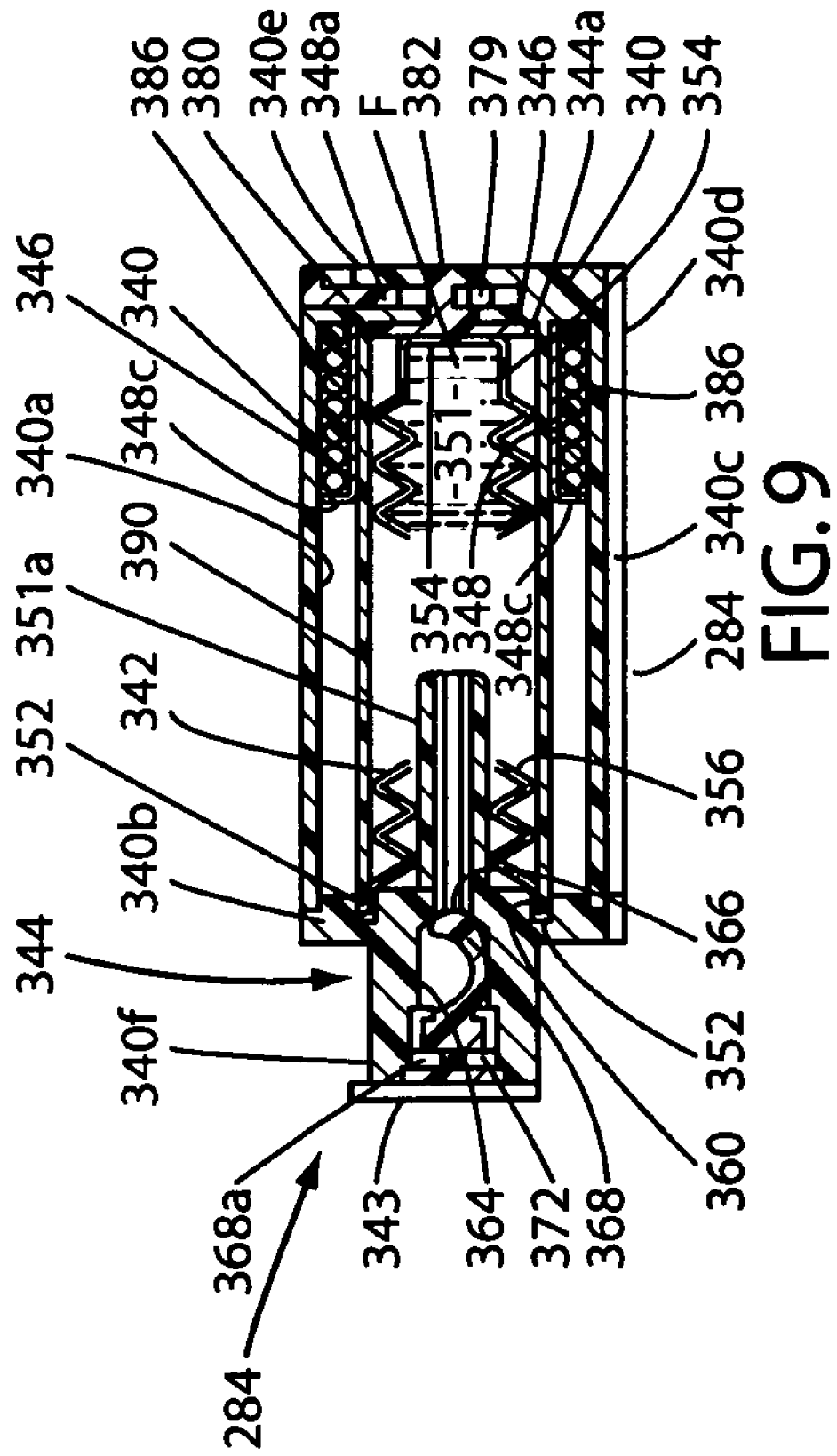
FIG. 9 is a longitudinal, cross-sectional view of the additive sub-system of the fluid dispensing device shown in FIG. 7.
Figure 10:
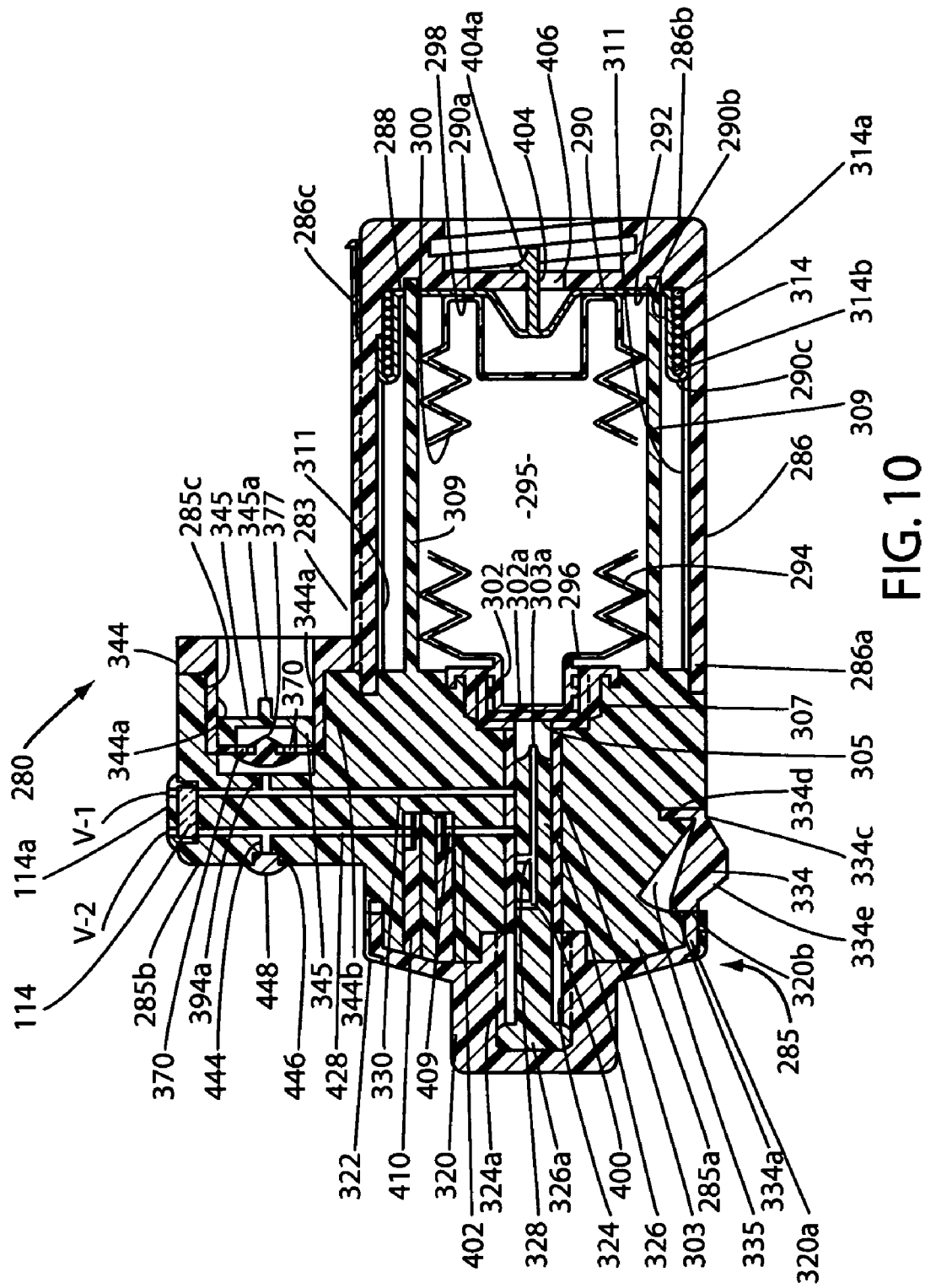
FIG. 10 is a longitudinal, cross-sectional view of the fluid dispenser portion of the device illustrated in FIG. 7.

Referring now to FIGS. 5 through 10, an alternate form of the dispensing device of the present invention for dispensing medicaments to a patient is there shown and generally designated by the numeral 280. The apparatus of this latest embodiment is similar to that previously described, but the dispensing device here comprises two major cooperating components, namely a dispenser unit 282 and a separate, stand-alone additive sub-system 284. Dispenser unit 282 includes an outer housing 283, which comprises a control portion 285 and a generally cylindrically shaped reservoir housing 286 that is interconnected with the control portion 285 in the manner best seen in FIG. 7 of the drawings. Additive sub-system 284, the details of construction and operation of which will presently be described, is also operably interconnected with the control portion 285 in the manner best seen in FIG. 7. As shown in FIGS. 7 and 10, reservoir housing 286, which can be constructed from metal, plastic or any suitable material, includes a generally cylindrically shaped wall portion 286a and a base portion 286b.

Figure 38:
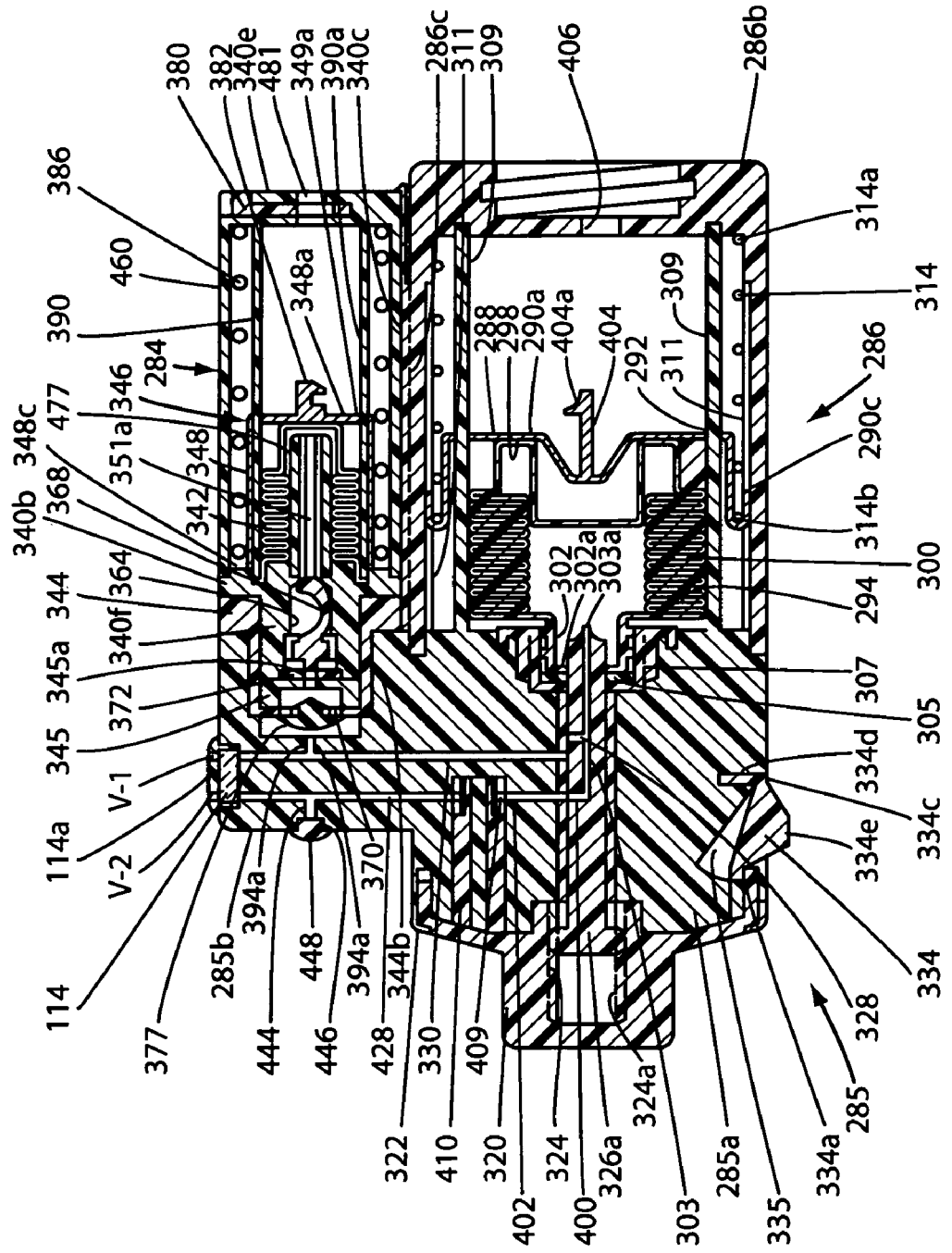
FIG. 38 is a longitudinal, cross-sectional view, similar to FIG. 32, but showing the configuration of the dispenser following expelling of the fluid from the fluid reservoir.
Figure 39:
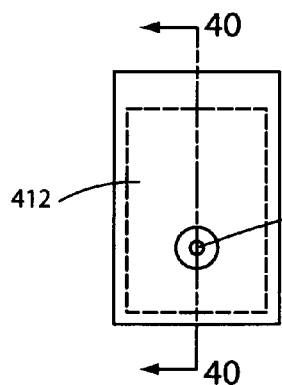
FIG. 39 is a front view of the rate control subassembly of the dispenser portion of the device.

Disposed within wall portion 286a is a carriage assembly 288 (FIGS. 7, 8 and 10), which is movable between a first position shown in FIG. 7 and a second position shown in FIG. 38. As best seen by referring to FIG. 8, carriage assembly 288 comprises a carriage having a carriage base 290a that is provided with a plurality of circumferentially spaced openings 292 and a generally cylindrically shaped sidewall 290b which terminates in circumferentially extending flange 290c. Carriage assembly 288 is releasably locked in its first position by a novel locking means the character of which will presently be described.

Figure 18:
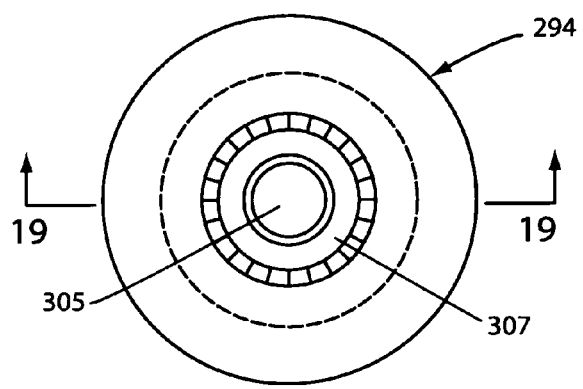
FIG. 18 is a top view of the reservoir housing of the fluid dispenser portion of the device.
Figure 20:
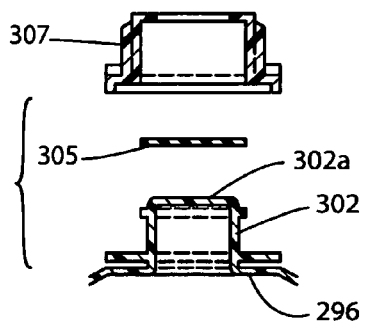
FIG. 20 is an exploded, cross-sectional view of the upper neck portion of the reservoir housing of the fluid dispenser portion of the device shown in FIG. 19.
Figure 19:
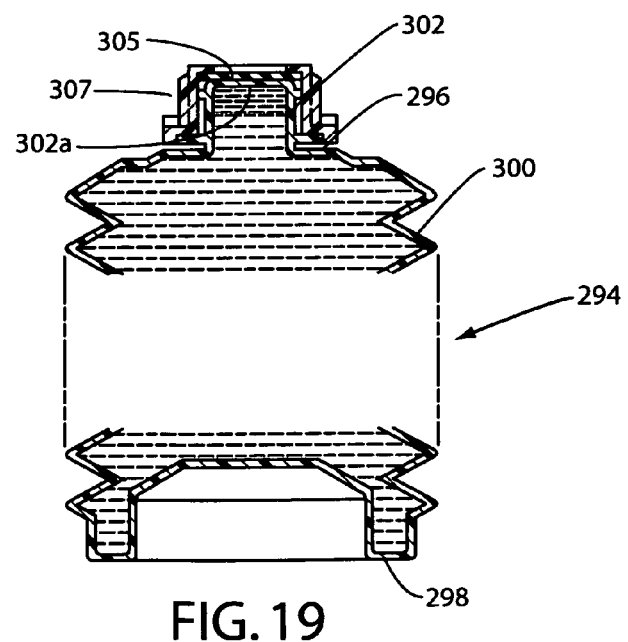
FIG. 19 is a cross-sectional view taken along lines 19-19 of FIG. 18.

Carried by carriage assembly 288 is a reservoir-defining assembly 294 that defines a fluid reservoir 295. As indicated in FIGS. 18, 19 and 20, reservoir-defining assembly 294 comprises a top wall 296, a bottom wall 298 and an accordion-like sidewall 300. Connected to top wall 296 is a neck portion 302 that is sealed by a closure wall 302a (FIGS. 19 and 20).

In the preferred form of the invention, reservoir-defining assembly 294 is formed in accordance with an aseptic blow-fill seal technique which is of a character well understood by those skilled in the art. This technique involves the continuous extrusion through an extruder head of a length of parison in the form of a hollow tube between and through two co-acting first or main mold halves. The technique further includes the step of cutting off the parison below the extruder head and above the main mold halves to create an opening which allows a blowing and filling nozzle assembly to be moved downwardly into the opening in the parison for molding the molded container.

In a manner presently to be described, the collapsible container is accessible via a penetrating member 303 that is adapted to pierce closure wall 302a as well as a pierceable membrane 305 (FIGS. 18 and 19) which is positioned over closure wall 302a of by means of a closure cap 307 which is affixed to the neck portion 302 of container assembly 294 (FIG. 19). As previously described, the basic container 294 is formed using the earlier described aseptic blow-fill technique and the reservoir portion of the container is sealed by the thin closure wall 302a. The piercable membrane 305 is then positioned over the closure wall and the closure cap 307 is positioned over the piercable membrane and secured to neck portion 302 by any suitable means such as adhesive bonding or sonic welding.

An important feature of the invention resides in the provision of novel guide means for guiding travel of carriage assembly 288 between the first position shown in FIG. 7 and the second position shown in FIG. 38. In the present form of the invention this important guide means comprises a plurality of circumferentially spaced guide members 309 which are connected to and extend outwardly from body 285a of control portion 285 (FIGS. 7 and 8). As indicated in the drawings, guide members 309 are slidably received within openings 292 provided in carriage base 290a (FIG. 8) so that as the carriage assembly travels from its first position toward its second position, guide members 309 precisely guide its travel. Also forming a part of the guide means of the apparatus of the present invention are a plurality of circumferentially spaced guide grooves 311 that are formed on the inner wall of outer housing 286 (FIG. 7).

To controllably move the carriage assembly from its first position to its second position, novel stored energy means are provided. This stored energy means, which is operably associated with carriage assembly 288, is here provided in the form of a coiled spring 314. As illustrated in FIGS. 7 and 10, one end 314a of the coil spring 314 is disposed in engagement with the threaded base portion 286b of reservoir housing 286 and the other end 314b thereof is disposed in engagement with radially outwardly extending flange segments 290c of carriage 288. With this construction, when, as will presently be described, the operating means of the invention has been operated in a manner to place the device in the fluid delivery mode and when the locking means of the invention is manipulated in a manner to unlock the carriage assembly from base portion 286b of the outer housing, spring 314 will move from its retracted position shown in FIG. 7 to its expanded position shown in FIG. 38. As the spring moves toward its expanded position it will controllably move the carriage assembly from its starting position shown in FIG. 7 to its fully deployed, or extended position shown in FIG. 38. As will be described more fully in the paragraphs which follow, as the carriage assembly moves toward its deployed position, the accordion-like side wall 300 of the reservoir-defining container will move into the collapsed configuration shown in FIG. 38 and in so doing will cause the medicinal fluid contained within the container to be controllably expelled therefrom.

To control the flow of medicinal fluid from the reservoir 295 toward the administration set 318 of the invention (FIG. 5), novel flow control means are provided. This novel fluid flow control means, which is housed within the control portion 285 of the device, here comprises two cooperating components, namely a rate control means for controlling the rate of fluid flow from the collapsible reservoir toward the administration set and the previously mentioned operating means for controlling fluid flow into and out of the fluid reservoir 295.

Figure 21:
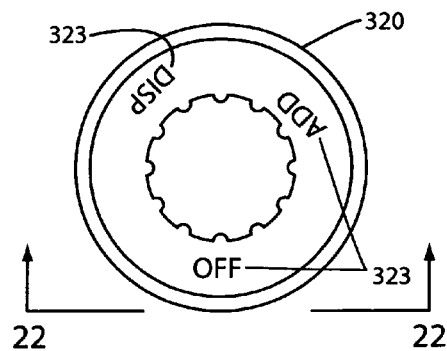
FIG. 21 is a top view of the rate control knob of the fluid dispenser portion of the device.
Figure 22:
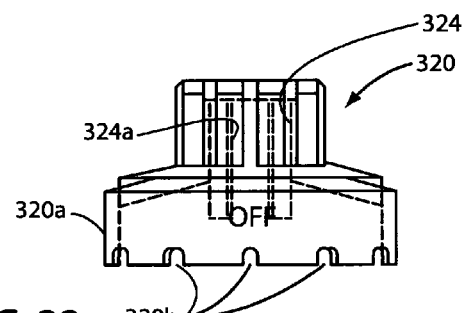
FIG. 22 is a view taken along lines 22-22 of FIG. 21.
Figure 24:
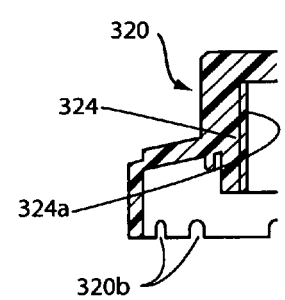
FIG. 24 is a cross-sectional view taken along lines 24-24 of FIG. 23.
Figure 25:
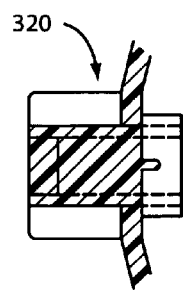
FIG. 25 is a cross-sectional view taken along lines 25-25 of FIG. 23.
Figure 23:
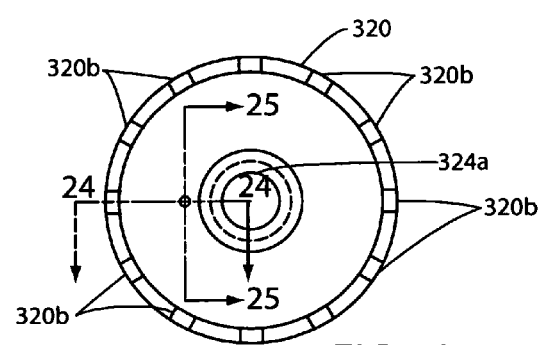
FIG. 23 is a bottom view of the rate control knob of the fluid dispensing portion of the device.

Considering first the operating means of the invention, this important means, here comprises reservoir accessing means for accessing the fluid reservoir 295 that includes a control knob 320 (FIGS. 5, 7, 8, 10, 21 and 22) that is rotatably mounted on body 285a of control portion 285 and penetrating means for penetrating both membrane 305 as well as closure wall 302a of the reservoir container. As best seen in FIGS. 7 and 8, the control knob 320 is held in position on body 285a by a knob retaining ring 322. Control knob 320, which is provided with control indicia 323 (FIG. 21), has an axial bore 324 having threads 324a that threadably receive the head portion 326a of an elongated needle housing 326 that carries penetrating member 303 of the previously identified penetrating means of the invention (FIGS. 7, 8 and 22). With this construction, an initial rotation of knob 320 will cause the needle housing 326 to controllably move from the position shown in FIG. 7 to the position shown in FIG. 32, wherein fluid passageway 328 aligns with passageway 330 formed in control body portion 285a.

As indicated in FIG. 32, rotation of control knob 320 will also cause penetrating member 303 to pierce both membrane 305 as well as closure wall 302a of the reservoir container. With the additive sub-system 284 interconnected with the dispenser unit in the manner shown in FIG. 7, this movement of the needle housing 326 and the penetrating member 303 opens fluid communication between the additive sub-system 284 and the fluid reservoir 295 via passageway 330, stub passageway 328 and the internal fluid flow passageway 303a of penetrating member 303.

To prevent accidental rotation of control knob 320, indexing means, here provided in the form of an indexing button 334, functions to prevent rotation of the control knob until the indexing button, which is pivotally mounted on the side of the control portion of the device (FIGS. 7 and 8), is pivoted inwardly of a cavity 335 formed in body 285a of control portion 285. As illustrated in FIGS. 8 and 22 of the drawings, the skirt portion 320a of the control knob is provided with a plurality of circumferentially spaced notches 320b that closely receive a locking tab 334a (FIG. 8), formed on indexing button 334 when the button is biased toward its outward locking position shown in FIG. 7 by a living hinge 334c that interconnects a finger 334d with the body portion 334e of the indexing button (FIG. 8). To accomplish the initial rotational step, described in the preceding paragraph, the indexing button 334 is pushed inwardly to move the locking tab 334a out of engagement with the notch within which it resides and the control knob is rotated from the "OFF" position (FIG. 21) to the "ADD" position. Release of the indexing button will then cause the outwardly biased locking tab 334a to move into engagement with an appropriate locking notch so as to lock the control knob in the "ADD" position.

Figure 11:
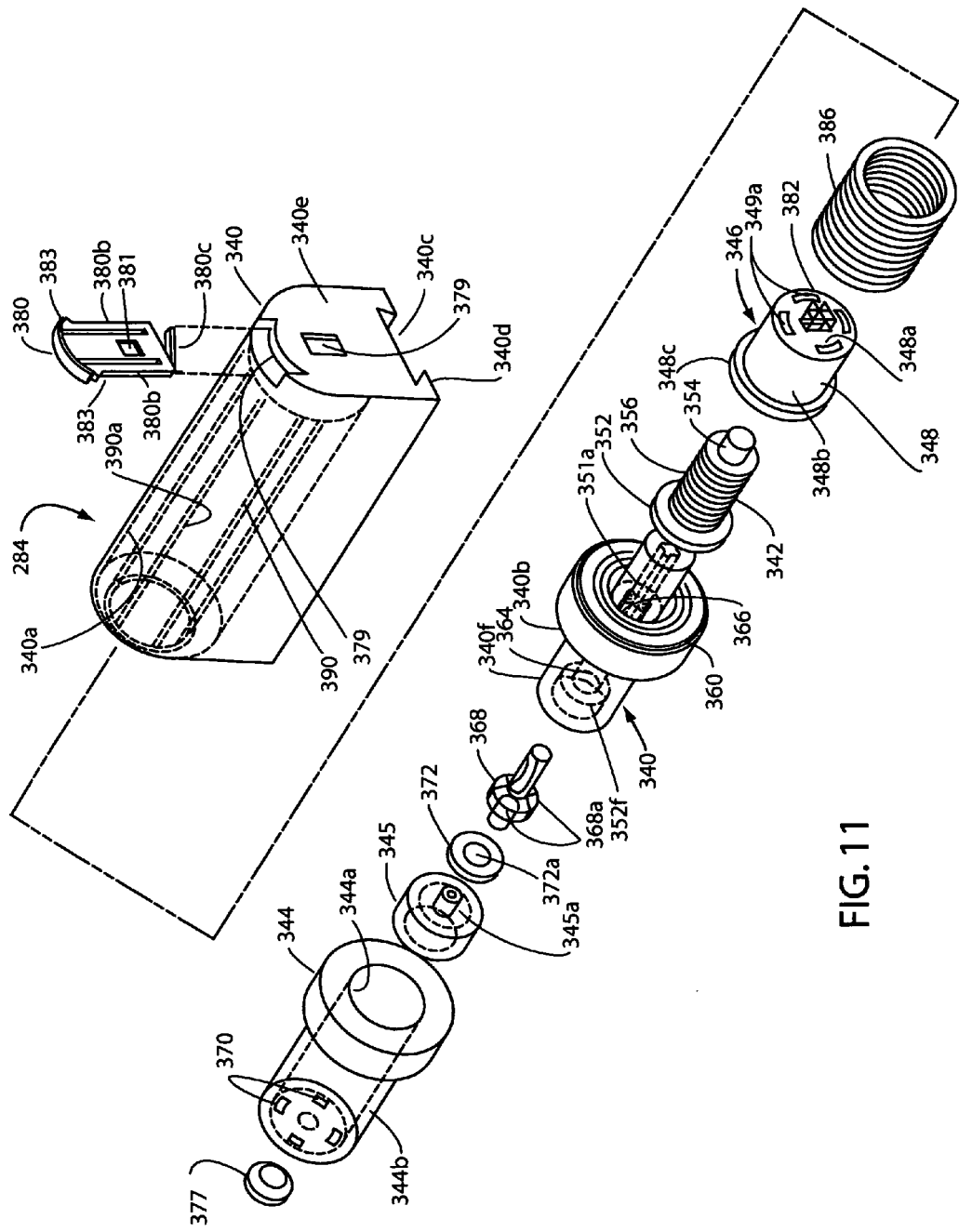
FIG. 11 is a generally perspective, exploded view of the additive sub-system of the fluid delivery dispenser illustrated in FIG. 9.

Considering now the details of the construction and operation of the form of the additive sub-system shown in FIGS. 9, 11 and 12 and generally designated by the numeral 284; this important additive sub-system here comprises a vial housing 340 having a chamber 340a for telescopically receiving the novel medicament containing, bellows-type, collapsible fill-vial 342. Chamber 340a is initially sealed at one end by a seal cover 343 and at the other end by an end wall 340e. In the present form of the invention, dispenser reservoir 295 and medicament containing vial of the vial assembly 340 can be of various volumes ranging from about 5 ml to about 50 ml.

As shown in FIGS. 7 and 8, vial housing 340 has a forward wall 340b that includes a generally cylindrical, forwardly extending portion 340 that is receivable within an internal chamber 344a formed in a check valve housing 344. Check valve housing 344 has a forwardly extending portion 344b that is receivable within an internal chamber 285c formed in connector control portion 285. Mounted within internal chamber 344a of the check valve housing is a check valve actuator 345 the construction and operation of which will later be described.

Formed in the lower surface 340d of connector housing 340 is a dove tail receiving groove 340c (FIGS. 8 and 11), the purpose of which will presently be described. Also forming a part of the additive sub-system 284 of the invention is a carriage assembly 346 (FIGS. 9, 11 and 12), which is movable between a first position shown in FIGS. 7 and 9 to a second position shown in FIG. 32. Carriage assembly 346 here comprises a carriage 348 having a carriage base 348a having a plurality of circumferentially spaced openings 349a and a generally cylindrically shaped sidewall 348b which terminates in a circumferentially extending flange 348c. Carriage assembly 346 is releasably locked in its first position by a novel locking means the character of which will presently be described.

Carried by carriage assembly 346 is the previously identified bellows-type, collapsible fill-vial 342 that defines a fluid reservoir 351. As indicated in FIG. 12 fill-vial 342 comprises a flange portion 352, a closure wall 354 and an accordion-like sidewall 356. In the preferred form of the invention, the bellows-type, collapsible fill-vial 342 is blow-molded in a manner well understood by those skilled in the art.

Flange portion 352 of the vial 342 is closely receivable within an annular groove 360 formed in forward wall 340b of additive housing 340. As indicated in FIG. 12 of the drawings, the generally cylindrical portion 340f of the forward wall, which here comprises a main check valve housing, is provided with an internal chamber 364 that is in communication with the fluid reservoir 351 via an inlet port 366. Connected to forward wall 340b and extending into fluid reservoir 351 is an ullage member 351a, the purpose of which will presently be described.

Mounted within the chamber 364 of the main check valve housing is a novel yieldably deformable check valve 368 that functions to prevent fluid flow outwardly of fluid reservoir 351 until the additive sub-system 284 is interconnected with the dispenser unit 285. More particularly, as the additive sub-system is mated with the dispenser unit, check valve 368 will be deformed by the neck portion 345a of the actuator member 345 (FIG. 32) from the first sealing configuration shown in FIG. 36 wherein the fluid flow from reservoir 351 is blocked from flowing through the fluid passageways 370 formed in portion 344b by the sealing shoulders 368a of the check valve 368 which are in sealing engagement with the check valve retainer member 372 to the second configuration shown in FIGS. 34 and 37. As indicated in FIG. 37, as the additive sub-system is mated with the dispenser unit, the neck portion 345a of the valve actuator 345 will urge the check valve 368 inwardly in a manner such that the sealing shoulders 368a of the check valve 368 will be separated from the check valve retainer member 372 thereby permitting fluid flow through the fluid passageway 372a in the direction of the arrows 373.

The reservoir fill step for filling reservoir FIG. 37 from the additive subsystem 295 of the dispenser 285 is accomplished by first removing sterile cover 343. Next, the additive sub-system 284 of the device is interconnected with the control portion 285 of the dispenser unit in the manner illustrated in FIG. 7. More particularly, as shown in FIGS. 8 and 11, reservoir housing 286 is provided with a dovetail connector segment 286c that is slidably received within the groove 340c formed in connector housing 340.

As indicated in FIG. 7, when the dovetail connector segment 286c is mated with and urged forwardly of the dovetail receiving groove 340c formed in connector housing 340, cylindrical portion 340f of front wall 340b will be telescopically received and seated within internal chamber 344a of connector portion 344.

When the dovetail connector segment 286c is mated with and urged forwardly of the dovetail receiving groove 340c formed in connector housing 340, cylindrical portion 340f of front wall 340b will be telescopically received and seated within internal chamber 344a of connector portion 344 and the check valve will be deformed in a manner previously described so that the sealing shoulders 368a of the check valve 368 will be separated from the check valve retainer member 372. With the additive sub-system thusly interconnected with the dispenser component, the carriage lock 382, which is carried within a slot 379 formed in end wall 340e of housing 340, is manipulated in a manner to release carriage 346. More particularly, as best seen and FIGS. 26 through 31, carriage lock 380 comprises a central body portion 380a to which a pair of spaced-apart, yieldably deformable side members 380b and a yieldably deformable bottom member 380c are connected. Bottom member 380c continuously urges the carriage lock 380 toward the at-rest position shown in FIG. 29. Central body portion 380a is provided with an opening 381 that is adapted to receive the hook-like locking protuberance 382 that is connected to and extends outwardly from base wall 348a of the carriage assembly 346. When the carriage lock 380c is in its at-rest position shown in FIG. 29 of the drawings, the locking elements 383 formed at the extremities of side members 380b are retained within locking slots 385 formed in wall 340e. When a downward force is exerted on the locking member, the side members 380b, along with bottom member 380c will be yieldably deformed in the manner shown in FIG. 31 of the drawings. This downward movement of the carriage lock from the at-rest locking position shown in FIG. 29 to the downward position shown in FIG. 31 will cause the opening 381 to move downwardly a sufficient distance to release the hook-like protuberance in the manner shown in FIG. 30.

Release of the hook-like protuberance 382 will permit the coiled spring 386, which is carried within housing 340 in the manner shown in FIGS. 28 and 30, to urge the carriage assembly 346 forwardly of housing 340 from the position shown in FIG. 28 the position shown in FIG. 30. Forward movement of the carriage will be guided by the plurality of spaced-apart guide members 390 that are mounted within the housing 340 and are received within the circumferentially spaced slots 349a formed in carriage base 348a. As the carriage moves forwardly the bellows-like sidewall of the fluid containing vial 342 will collapse in the manner shown in FIG. 37 of the drawings causing the fluid contained within vial reservoir 351 to be urged outwardly thereof via fluid passageways 345a (FIG. 34) and in the direction of the arrow 391 of FIG. 37. The ullage 351a functions to ensure that substantially all of the fluid contained within reservoir 351 will be expelled therefrom.

The fluid flowing from vial reservoir 351 will flow past main check valve 368, through the fluid passageways 370 in the direction of the arrows 391 and 373 and around and about an umbrella check valve 377 that is carried by check valve housing 344. The fluid flowing around and about an umbrella check valve 377 in the direction of the arrows 373 of FIG. 37 will then flow into fluid passageway 330 that is formed in dispenser housing portion 285c via a stub passageway 394a.

From passageway 330, the fluid will flow into inlet passageway 328 and then into reservoir 295 of the container via the central passageway 303a of penetrating member 303. During the adding process, any gases trapped within the flow passageways of the device are vented to atmosphere via a vent "V-1" formed in connector portion 285c of control portion 285. Following the completion of the adding process as described in the preceding paragraphs wherein the fluid medicament "F" contained within vial reservoir 351 is added to the reservoir 295, the operating means is used to control the flow of the fluid mixture from the collapsible reservoir toward the rate control means and then onward toward the administration set. More particularly, to accomplish this fluid dispensing step, the indexing button 334 is once again pushed inwardly of cavity 335 to move the locking tab 334a out of engagement with the notch within which it resides and the control knob is rotated from the "ADD" position (FIG. 21) to the "DISP" position. Release of the indexing button will then cause the outwardly biased locking tab 334a to move into engagement with an appropriate locking notch so as to lock the control knob in the "ADD" position.

Further rotation of control knob 320, will also cause penetrating member 303 to move further inwardly to the position illustrated in FIG. 38, wherein a stub passageway 400 formed in penetrating member 303 aligns with a fluid flow passageway 402 formed in control portion 285a. With the penetrating member 303 in this advanced position fluid communication between the fluid reservoir 295 and the rate control means of the device is established via fluid flow passageway 303a of penetrating member 303.

To cause the fluid to flow from reservoir 295 toward the flow rate control means, the locking means of the invention must be manipulated in a manner to release the carriage assembly from base wall 286b of reservoir housing 286. In this regard, as best seen in FIGS. 7, 8, 10 and 38, the carriage locking means includes a locking member 404 having a yieldably deformable locking tab 404a which extends through a strategically shaped opening 406 provided in the base wall 286b of reservoir housing (see FIGS. 8 and 38). With this construction, an inward force exerted on the locking member will deform the locking tab 404 in a manner to permit it to pass through the opening 406 and in so doing release the carriage from the base wall 286b. Release of the carriage will permit the stored energy means, or coiled spring 314, to move the carriage from a position shown in FIGS. 7 and 10 into the position shown in FIG. 38.

As the accordion-like sidewall of the container collapses due to the urging of the coiled spring, the medicinal fluid mixture contained within the reservoir 295 will be controllably expelled therefrom and will flow toward the fluid passageway 303a of penetrating member 303, which has now moved into the position shown in FIG. 38 of the drawings. From the fluid passageway of penetrating member 303, fluid will flow into a stub passageway 400 into passageway 402 and then into the inlet 409 of the fluid rate control means of the invention.

Figure 40:
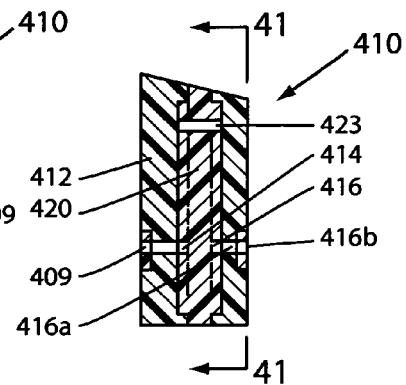
FIG. 40 is a cross-sectional view taken along lines 40-40 of FIG. 39.
Figure 41:
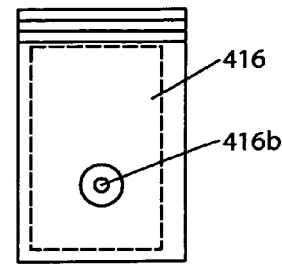
FIG. 41 is a view taken along lines 41-41 of FIG. 40.
Figure 42:
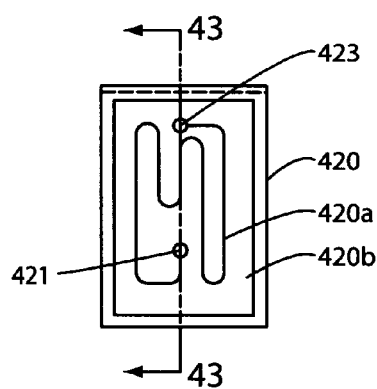
FIG. 42 is a front view of the rate control plate of the rate control subassembly shown in FIG. 40 of the drawings.
Figure 43:
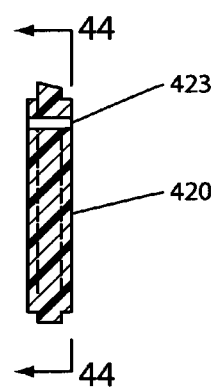
FIG. 43 is a cross-sectional view taken along lines 43-43 of FIG. 42.
Figure 44:
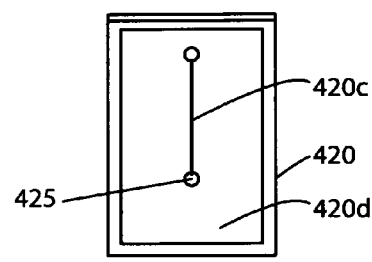
FIG. 44 is a view taken along lines 44-44 of FIG. 43.
Figure 49:
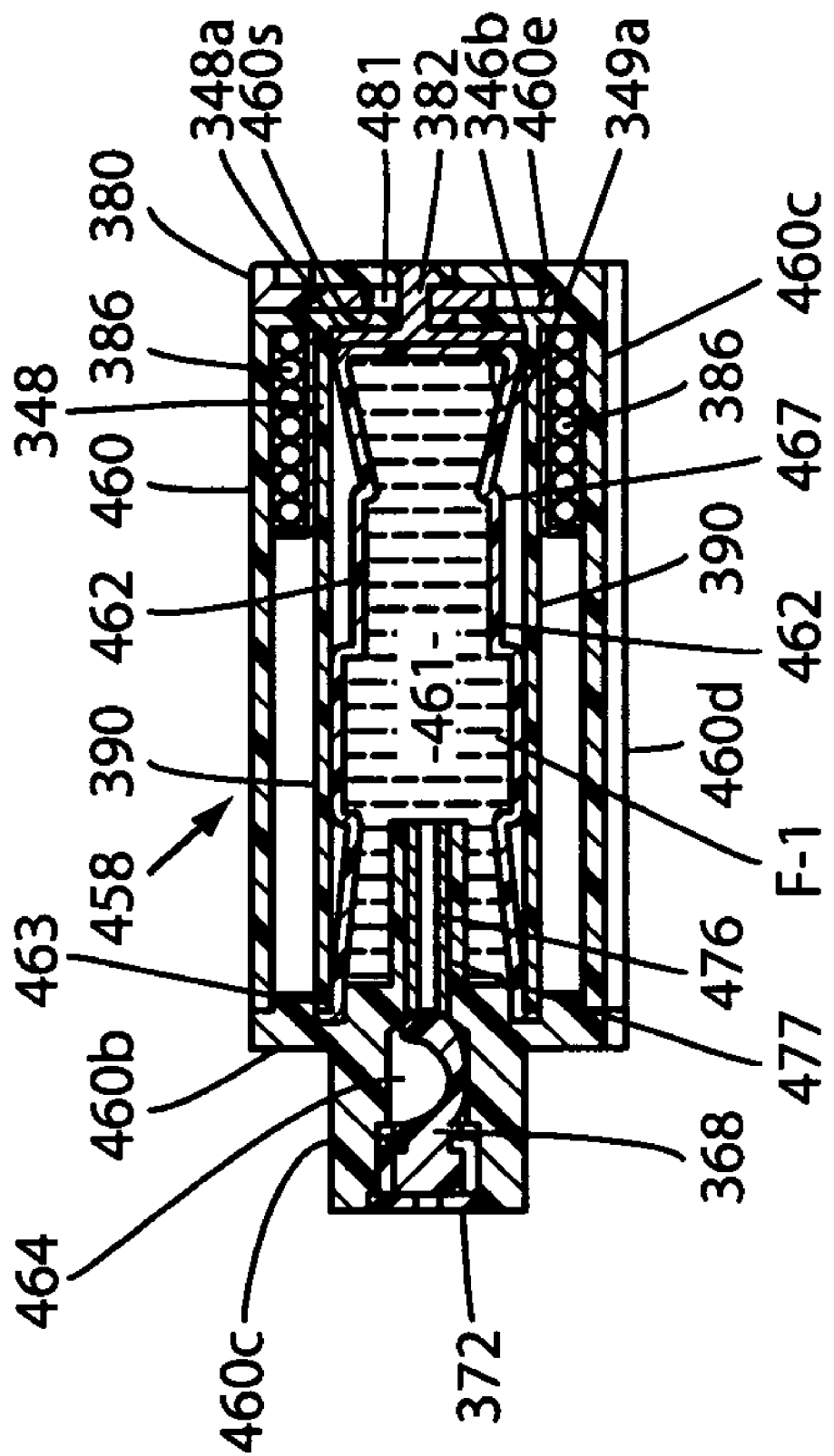
FIG. 49 is a longitudinal, cross-sectional view of another form of the additive sub-system of the invention.

The important fluid rate control means of the invention, which is illustrated in FIGS. 40 and 41 of the drawings, comprises a rate control housing 410, which includes a front cover 412 having the previously identified inlet 409 and an outlet 414. Rate control housing 410 also includes a back cover 416 having an inlet 416a and an outlet 416b. Disposed between the front and back cover is a novel rate control plate 420 having a uniquely configured, circuitous fluid flow channel 420a formed on the first surface 420b thereof and a substantially linear fluid flow channel 420c formed on the second surface 420d thereof (FIGS. 42-44).

With the construction described in the preceding paragraphs, as the sidewall of the fluid container collapses (FIG. 38), fluid will flow from reservoir 295 into the flow passageway of penetrating member 303, into stub passageway 400, then into passageway 402 and then into the inlet passageway 409 of the rate control means. From passageway 409, the fluid will flow into the front cover 412, through the outlet 414 and then into inlet 421 of fluid flow channel 420a. The fluid will then flow through the rate control channel, out the outlet 423 of the rate control channel and into the inlet 416b of back cover 416, outwardly into substantially linear fluid flow channel 420c formed on the second surface 420d of rate control plate 420, out through outlet 425 thereof, out through outlet 414 of back cover 416 and then into an elongated passageway 428 formed in the connector portion 285c of control portion 285. From the elongated channel 428 the fluid will flow onward to the administration set 318 and then to the patient. It is apparent that by varying the geometry, including the length, width and depth of the flow control channels 420a and 420c, the rate of fluid flow to the administration set and to the patient can be readily varied. During the fluid dispensing process, any gases trapped within the fluid delivery passageways of the device are vented to atmosphere via a vent "V-2" formed in connector segment 285b.

As indicated in FIG. 5, administration set 318 is sealably connected to the control portion 285a by any suitable means so that the proximal end of the administration line 318a of the administration set is in communication with an outlet fluid passageway in communication with passageway 428. Disposed between the proximal end and the distal end of the administration line is a conventional clamp 435, a conventional gas vent and filter 437 and a conventional "Y" site 439. Provided at the distal end of the administration line is a luer connector 441 of conventional construction.

To accomplish residual drug recovery from reservoir 295 as may be required, recovery means are provided. In this regard, as best seen in FIGS. 7 and 38 a stub passageway 444 formed in body 285b also communicates with fluid passageway 428. Stub passageway 444 also communicates with a cavity 446 formed in body 285b (FIG. 38). Sealably mounted within cavity 446 is a pierceable septum 448 which is pierceable by the needle of a conventional syringe that can be used to accomplish residual drug recovery from reservoir 295.

As illustrated in FIGS. 5 and 8, housing 286 is provided with a belt clip receiving member 452 to which a belt clip 454 can be slidably interconnected. When the belt clip 454 is connected with receiving member 452, the device can be conveniently carried on the user's belt during the adding and medicament dispensing steps.

Referring to FIGS. 45 through 48, an alternate form of the fluid dispensing device of the present invention for dispensing medicaments to a patient is there shown. This alternate form of dispensing device is similar in many respects to that shown in FIGS. 5 through 44 and like numerals are used in FIGS. 45 through 47 to identify like components. The major difference between this latest embodiment of the invention and that shown in FIGS. 5 through 44 resides in the differently configured additive sub-system 458. The dispenser unit 282 of this latest embodiment of the invention is substantially identical in construction and operation to that previously described and the additive sub-system 458 is connected to the dispenser unit in substantially the same manner.

This important additive sub-system 458 here comprises a vial housing 460 having a chamber 460a for telescopically receiving the novel medicament containing, collapsible fill-vial 462. Collapsible fill-vial 462, rather than being of a bellows-type construction, here comprises a collapsible bottle-like construction. As before, dispenser reservoir 461 and medicament containing vial 462 can be of various volumes ranging from about 5 ml to about 50 ml.

As shown in FIG. 46, vial housing 460 has a forward wall 460b that includes a generally cylindrical, forwardly extending portion 460c that is receivable within internal chamber 344a formed in check valve housing 344. As before, check valve housing 344 has a forwardly extending portion 344b that is receivable within an internal chamber 285c formed in connector control portion 285b. Mounted within internal chamber 344a of the check valve housing is a check valve actuator 345 the construction and operation of which is identical to that previously described.

Formed in the lower surface 460d of connector housing 460 is a dovetail receiving groove 460e that mates with dovetail connector 286c in the manner previously described. Also forming a part of the additive sub-system 458 of this latest embodiment of the invention is a carriage assembly 346 which is substantially identical in construction and operation to that previously described and is movable between a first position shown in FIG. 46 to a second position shown in FIG. 47.

Carried by carriage assembly 346 is the previously identified bottle-like, collapsible fill-vial 462 that defines a fluid reservoir 461. As indicated in FIG. 46, fill-vial 462 comprises a flange portion 463, a closure wall 465 and a collapsible sidewall 467. In the preferred form of the invention, the collapsible fill-vial 462 is blow-molded in a manner well understood by those skilled in the art.

Flange portion 463 of the vial 462 is closely receivable within an annular groove 471 formed in forward wall 460b of connector housing 460. As indicated in FIGS. 46 and 47 of the drawings, the generally cylindrical portion 460c of the forward wall, which here comprises a main check valve housing, is provided with an internal chamber 464 that is in communication with the fluid reservoir 461 via an inlet port 476. Connected to forward wall 460b and extending into fluid reservoir 461 is an ullage member 477, the purpose of which will presently be described.

In carrying out the reservoir-filling step, the additive sub-system 458 of this latest form of the invention is interconnected with the control portion 285 by mating the dovetail connector segment 286c of the dispenser unit with the groove formed in connector housing 460 and then sliding the additive sub-system forwardly into the position shown in FIG. 46. As before, this step causes the check valve 368 to be moved from the reservoir sealing configuration shown in FIG. 45 to the configuration shown in FIGS. 46 and 47 where fluid is permitted to flow from the reservoir of the fill-vial toward the umbrella check valve 377.

Following the mating of the additive sub-system 458 with the dispenser unit, the carriage lock 482, which is carried within a slot 481 formed in end wall 460e of housing 460, is manipulated in the manner previously described to release carriage 346. More particularly, end wall 460e is provided with an opening 481 that is adapted to receive the hook-like locking protuberance 482 that is connected to and extends outwardly from base wall 346b of the carriage assembly 346. Accordingly, when the carriage lock 380 is manipulated in the manner previously described the hook-like protuberance will be released in the manner shown in FIG. 47.

Release of the hook-like protuberance 482 will permit the coiled spring 386, which is carried within housing 460, to urge the carriage assembly 346 forwardly of housing from the position shown in FIG. 46 toward the position shown in FIG. 47. Forward movement of the carriage will be guided by the plurality of spaced-apart guide members 390 that are mounted within the housing 460 and are received within the circumferentially spaced slots 349a formed in carriage base 346b. As the carriage moves forwardly the sidewall of the fluid containing vial 467 will collapse in the manner shown in FIG. 47 of the drawings causing the fluid contained within vial reservoir 461 to be urged outwardly thereof via fluid passageway 476 (FIG. 46) and in the direction of the umbrella valve 377. As before, the ullage 477 functions to ensure that substantially all of the fluid contained within reservoir 461 will be expelled therefrom.

The fluid flowing from vial reservoir 461 will flow past main check valve 368 and around and about the umbrella check valve 377. The fluid will then flow into fluid passageway 330 that is formed in dispenser housing portion 285b via a stub passageway 394a.

From passageway 330, the fluid will flow into inlet passageway 328 and then into reservoir 493 of the container via the central passageway 303a of penetrating member 303. During the adding process, any gases trapped within the flow passageways of the device are vented to atmosphere via a vent "V-1" formed in connector housing portion 285b of control portion 285. Following the completion of the adding process as described in the preceding paragraphs, wherein the fluid medicament "F-1" contained within vial reservoir 461 is added to the reservoir 493, the operating means is used in the manner previously described to control the flow of the fluid mixture from the collapsible reservoir 493 toward the rate control means and then onward toward the administration set.

Referring next to FIGS. 49 through 55, still another form of the fluid dispensing device of the present invention for dispensing medicaments to a patient is there shown. This latest form of dispensing device is similar in some respects to that shown in FIGS. 45 through 48 and like numerals are used in FIGS. 49 through 55 to identify like components. As before, this latest embodiment of the invention comprises two major cooperating components, namely a dispenser unit 490 and an additive sub-system 458. Additive sub-system 458 is substantially identical in construction and operation to that previously described in connection with the embodiment illustrated in FIGS. 45 through 48 and is connected to the dispenser unit in substantially the same manner.

The major difference between this latest embodiment of the invention and that shown in FIGS. 45 through 48 resides in the differently configured fluid container component 492 of the dispenser unit. This fluid container component, rather than being of a bellows-type construction, here comprises a collapsible bottle-like construction of the character best seen in FIG. 53 of the drawings.

As before, the reservoir 493 of the fluid container component 492 of the dispenser unit and medicament containing vial 462 of the additive sub-system can be of various volumes ranging from about 5 ml to about 50 ml.

Figure 50:
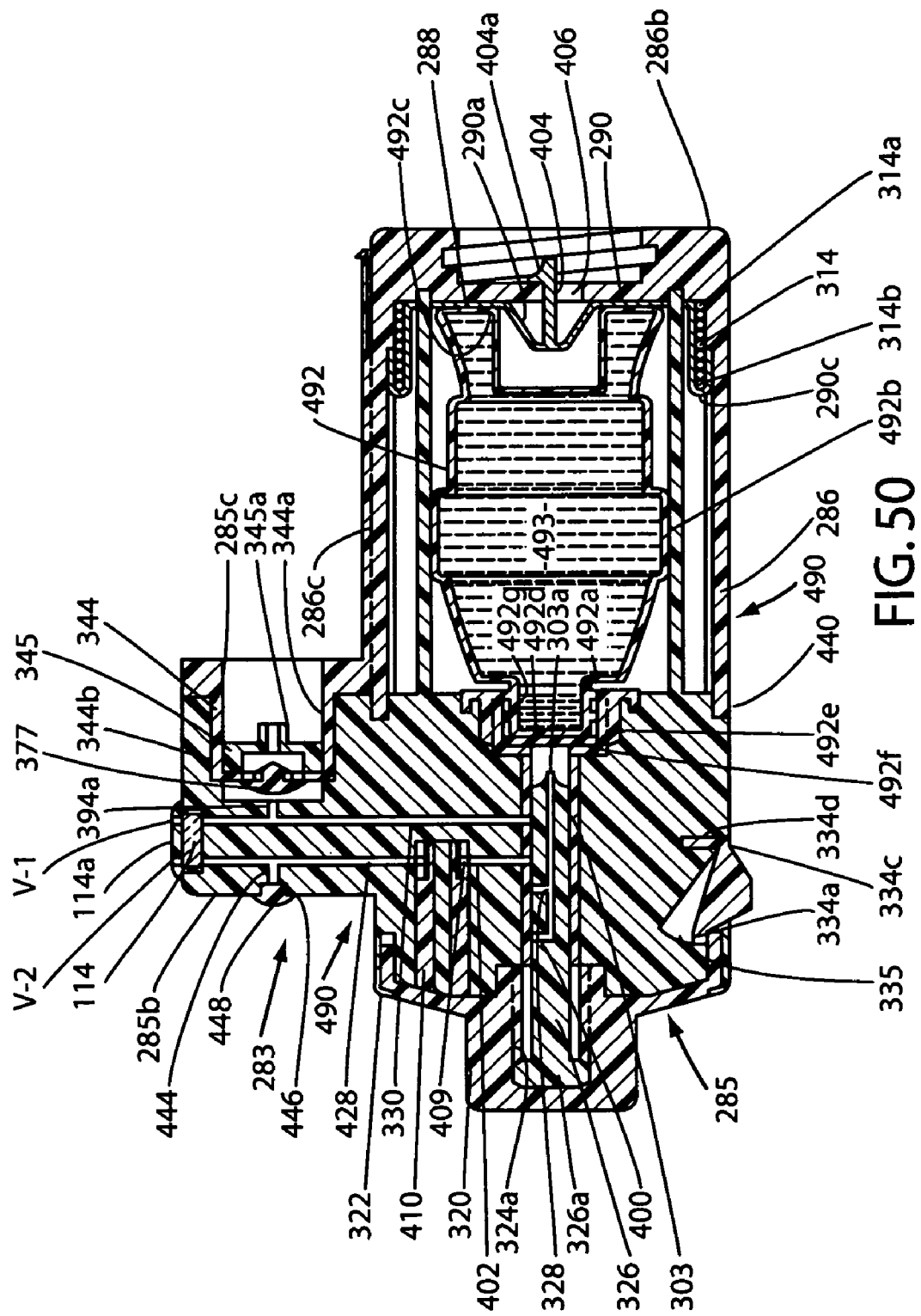
FIG. 50 is a longitudinal, cross-sectional view of the fluid dispenser portion of the device with which the additive sub-system illustrated in FIG. 49 can be mated.
Figure 51:
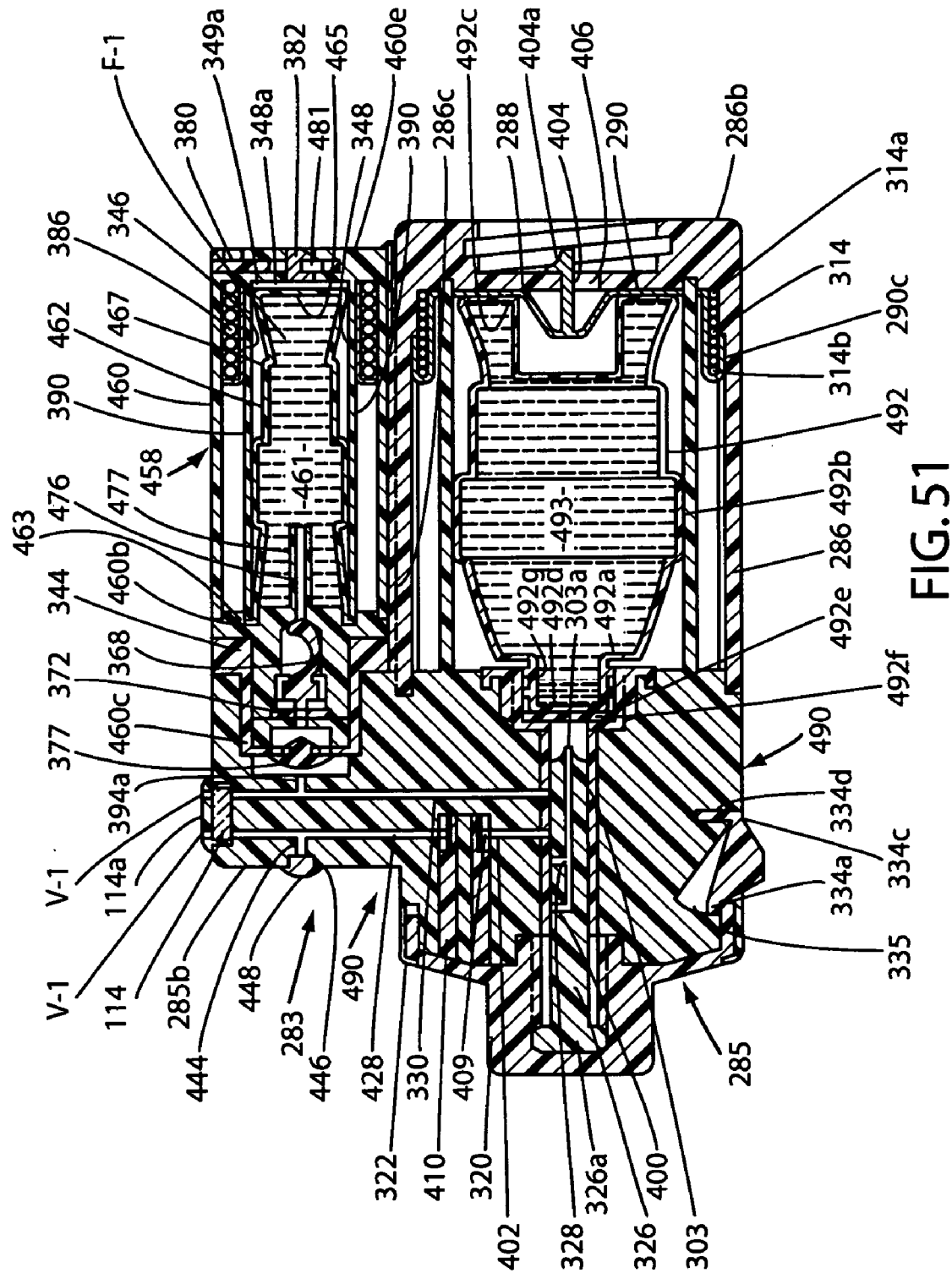
FIG. 51 is a longitudinal, cross-sectional view of the fluid dispenser portion of the device showing the additive sub-system illustrated in FIG. 49 mated therewith.

As illustrated in FIG. 50, the dispenser unit 490 is quite similar in construction to dispenser unit 282 and includes an outer housing 286, which comprises a control portion 285 and a generally cylindrically shaped reservoir housing 286 that is interconnected with the control portion 285 in the manner best seen in FIG. 51 of the drawings.

Housed within reservoir housing 286 is the differently configured fluid container component 492. As illustrated in FIGS. 50 and 52, the fluid container component 492 here comprises a bottle-like configuration having a top wall 492a, collapsible side wall 492b and an interconnected base 492c. Connected to top wall 492a is a neck portion 492g that is sealed by a closure wall 492d (FIGS. 53 and 54).

In the preferred form of the invention, reservoir defining assembly 492 is formed in accordance with an aseptic blow-fill technique of the character previously described. As before, reservoir defining assembly 492 is carried by a carriage assembly 288 which is of substantially identical construction and operation to that previously described.

In carrying out the reservoir-filling step, the additive sub-system 458 of this latest form of the invention is interconnected with the control portion 285 by mating the dovetail connector segment 286c of the dispenser unit with the groove 460c formed in connector housing 460 and then sliding the additive sub-system forwardly into the position shown in FIG. 51. As before, this step causes the check valve 368 to be moved from the reservoir sealing configuration to the configuration shown in FIG. 51 where fluid is permitted to flow from the reservoir of the fill-vial toward the umbrella check valve 377.

Following the mating of the additive sub-system 458 with the dispenser unit 490, the carriage lock 380, which is carried within a slot 460s formed in end wall 460e of housing 460, is manipulated in the manner previously described to release carriage 348. More particularly, end wall 460e is provided with an opening 481 that is adapted to receive the hook-like locking protuberance 382 that is connected to and extends outwardly from base wall 348a of the carriage assembly 346. Accordingly, when the carriage lock 380 is manipulated in the manner previously described the hook-like protuberance will be released in the manner shown in FIG. 55.

Figure 55:
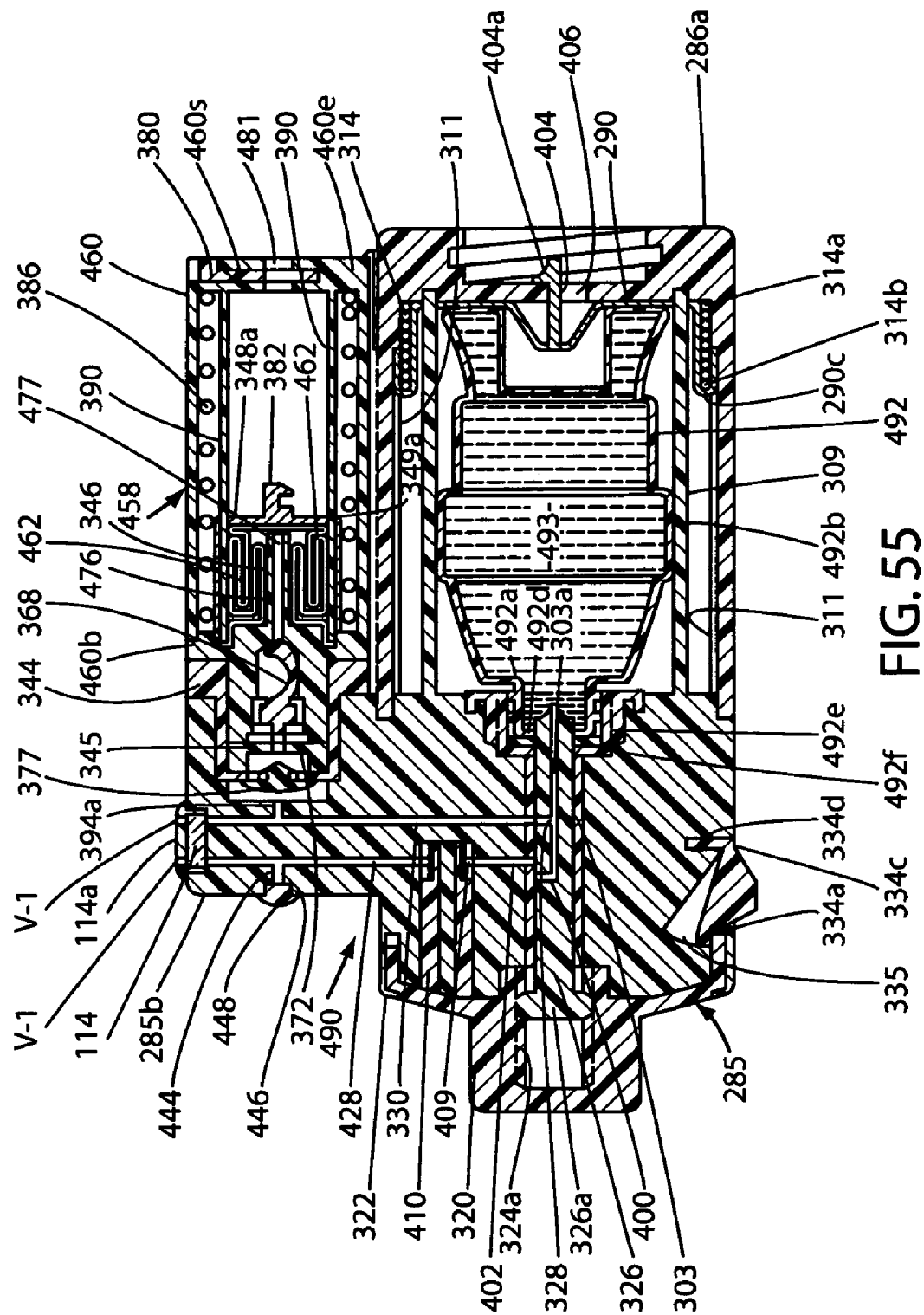
FIG. 55 is a longitudinal, cross-sectional view, similar to FIG. 51, but showing the fill-vial as it appears following filling of the reservoir of the dispenser unit portion of the device.

Release of the hook-like protuberance 382 will permit the coiled spring 386 to urge the carriage assembly 346 forwardly of housing from the position shown in FIG. 51 toward the position shown in FIG. 55. Forward movement of the carriage will be guided by the plurality of spaced-apart guide members 390 that are mounted within the housing 460 and are received within the circumferentially spaced slots 349a formed in carriage base 348a. As the carriage moves forwardly the sidewall of the fluid containing vial 462 will collapse in the manner shown in FIG. 55 of the drawings causing the fluid contained within vial reservoir 461 to be urged outwardly thereof via fluid passageway 476 (FIG. 55) and in the direction of the umbrella valve 377. As before, the ullage 477 functions to ensure that substantially all of the fluid contained within reservoir 461 will be expelled therefrom.

The fluid flowing from vial reservoir 461 will flow past main check valve 368 and around and about the umbrella check valve 377. The fluid will then flow into fluid passageway 330 that is formed in dispenser housing portion 285d via a stub passageway 394a.

From passageway 330, the fluid will flow into inlet passageway 328 and then into reservoir 493 of the container via the central passageway 303a of penetrating member 303. During the adding process, any gases trapped within the flow passageways of the device are vented to atmosphere via a vent "V-1" formed in connector housing portion 285b of control portion 285. Following the completion of the adding process as described in the preceding paragraphs, wherein the fluid medicament "F-1" contained within vial reservoir 461 is added to the reservoir 493, the operating means is used in the manner previously described to control the flow of the fluid mixture from the collapsible reservoir 493 toward the rate control means and then onward toward the administration set.

Figure 56:
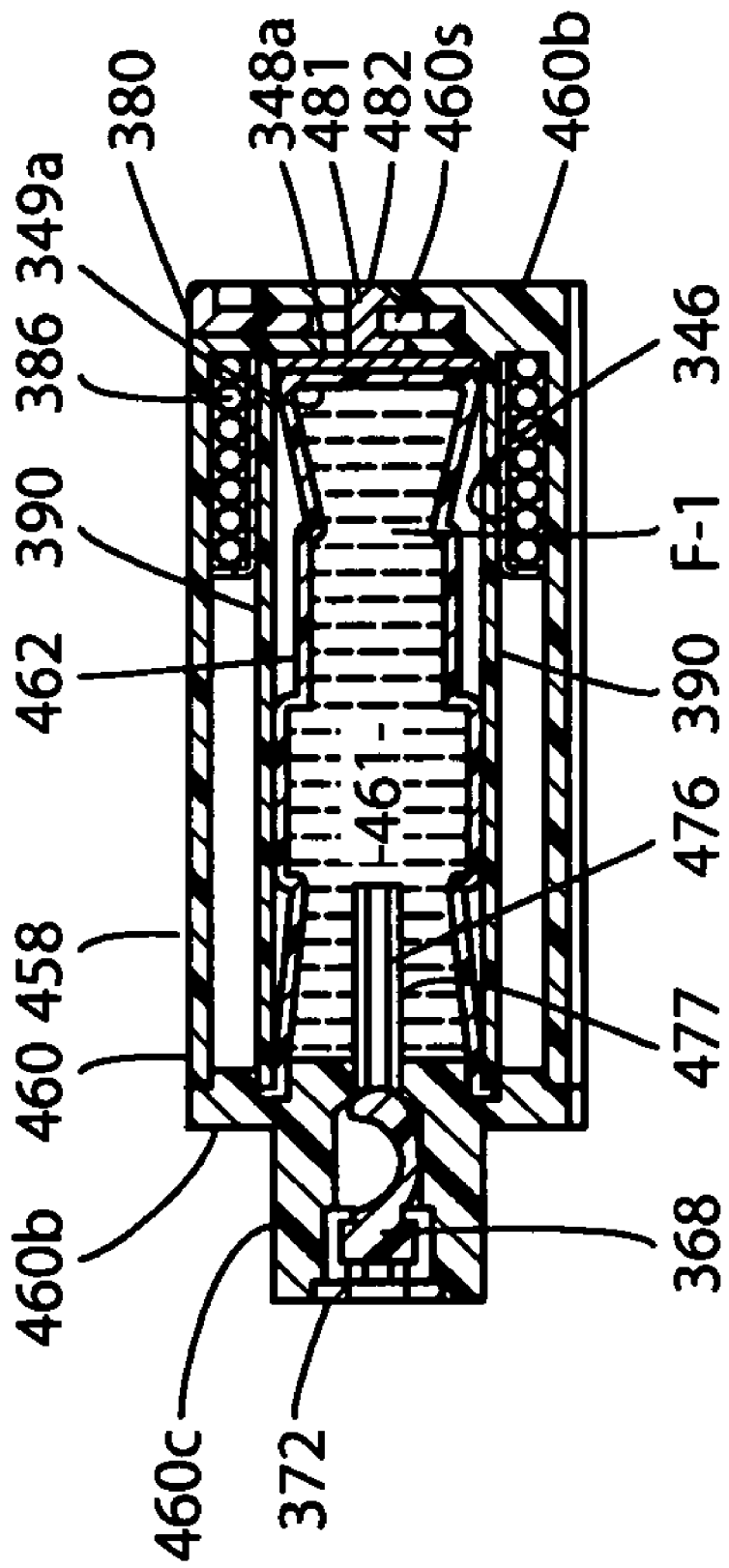
FIG. 56 is a longitudinal, cross-sectional view of the additive sub-system of the invention that is similar to the additive sub-system shown in FIG. 49.
Figure 57:
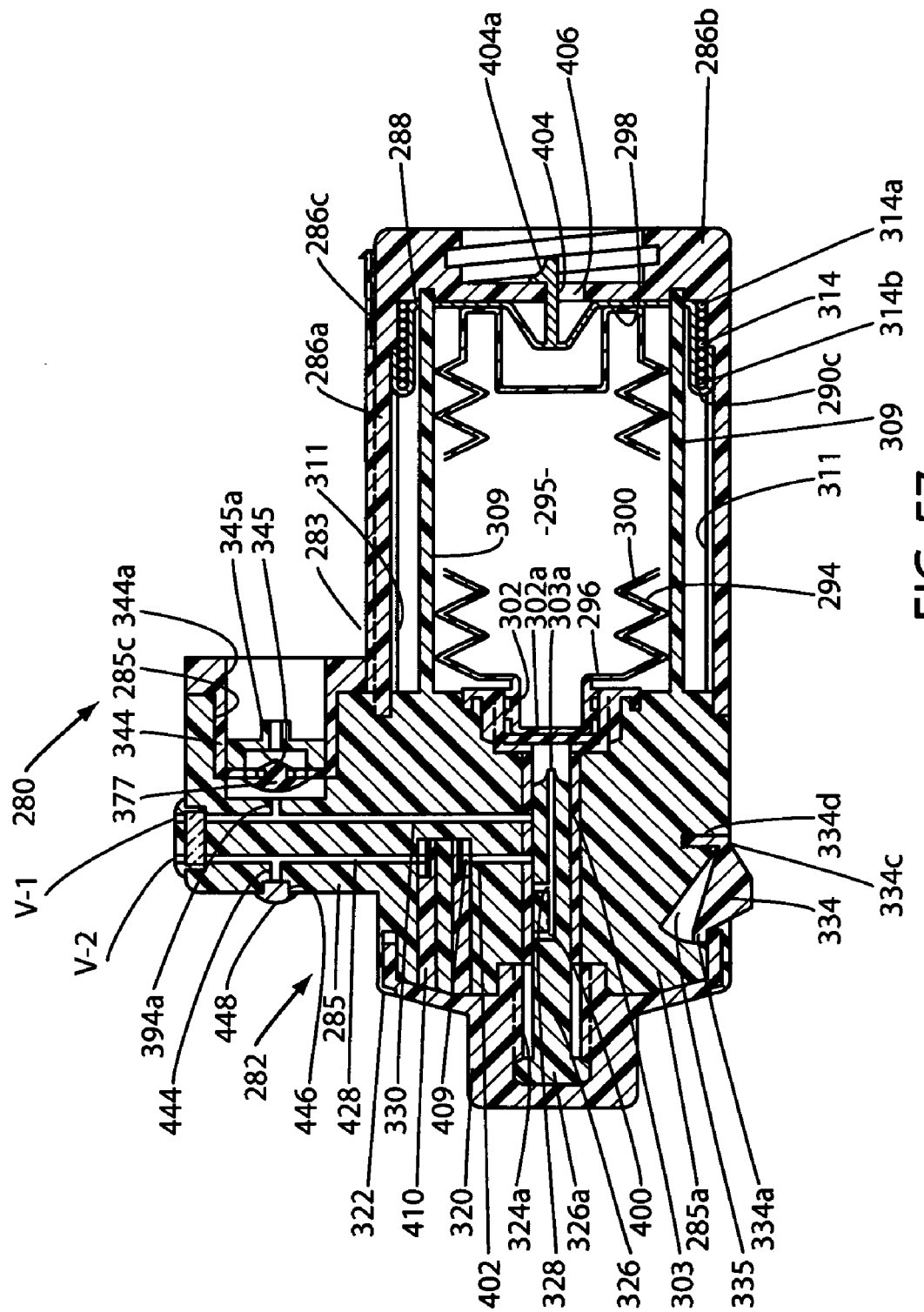
FIG. 57 is a longitudinal, cross-sectional view of the fluid dispenser portion of the device with which the additive sub-system illustrated in FIG. 56 can be mated.
Figure 58:
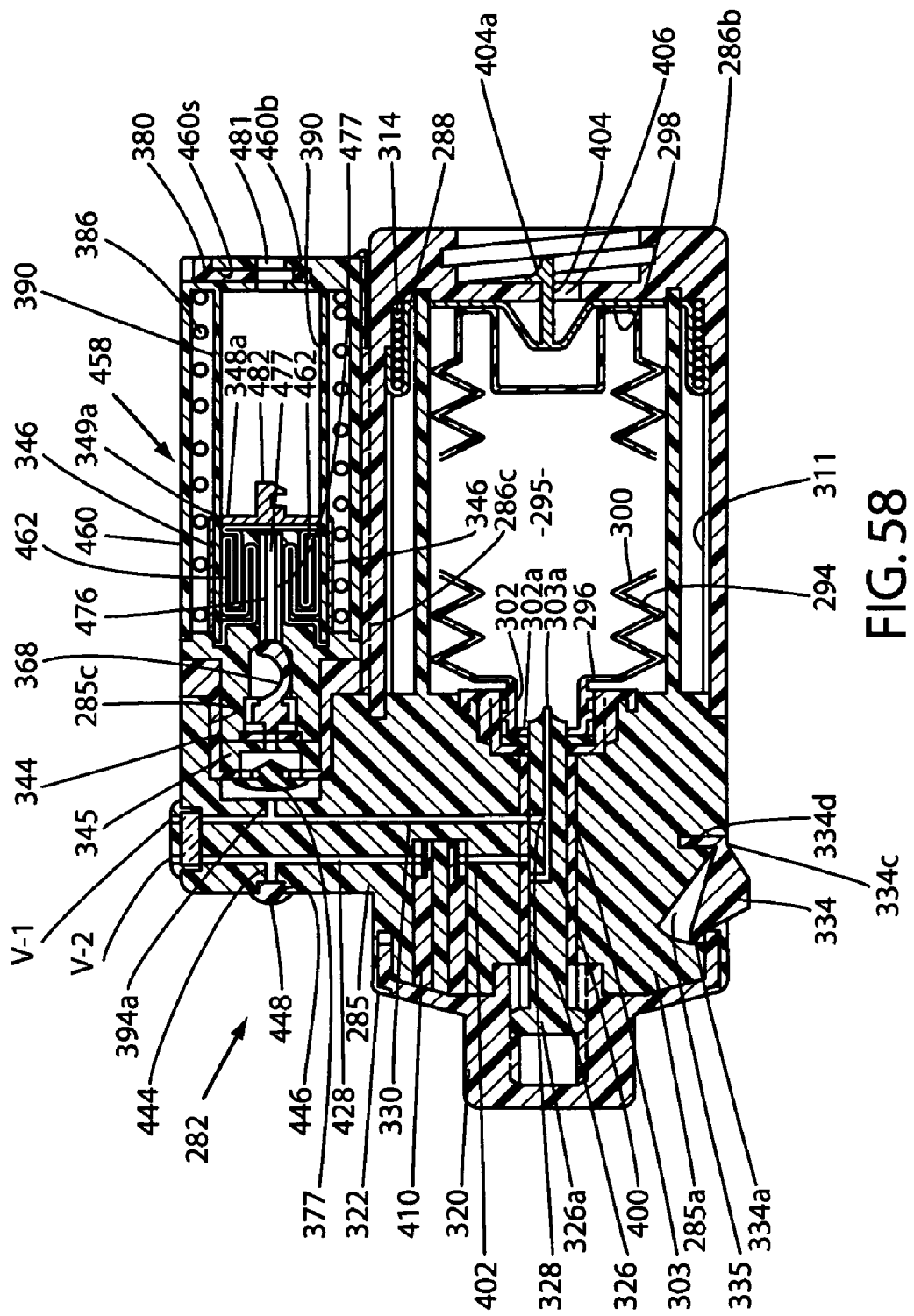
FIG. 58 is a longitudinal, cross-sectional view showing the additive sub-system illustrated in FIG. 56 mated with the dispenser unit, but showing the fill-vial as it appears following filling of the reservoir of the dispenser unit portion of the device.

Referring next to FIGS. 56, 57 and 58, still another form of the dispensing device of the present invention for dispensing medicaments to a patient is there shown. This alternate form of dispensing apparatus is similar in many respects to that shown in FIG. 51 and like numerals are used in FIGS. 56, 57 and 58 to identify like components. The major difference between this latest embodiment of the invention and that shown in FIG. 51 resides in the differently configured reservoir defining assembly. More particularly, the reservoir defining assembly 294 is substantially identical in construction and operation to that of the embodiment of the invention shown in FIGS. 18, 19 and 20. The additive sub-system 458 of this latest form of the invention is also substantially identical in construction and operation to that previously described and illustrated in FIG. 49 and includes a medicament containing, fill-vial assembly 462.

As was described in connection with the embodiment of FIGS. 18, 19 and 20, reservoir-defining assembly 294 comprises a top wall 296, a bottom wall 298 and an accordion-like sidewall 300. Connected to top wall 296 is a neck portion 302 that is sealed by a closure wall 302a (see also FIGS. 19 and 20).

In carrying out the reservoir-filling step, the additive sub-system 458 of this latest form of the invention is interconnected with the control portion 285 of the dispenser by mating the dovetail connector segment 286c of the dispenser unit with the groove formed in connector housing 460 and then sliding the additive sub-system forwardly into the position shown in FIG. 58. As before, this step causes the check valve 368 to be moved from the reservoir sealing configuration to the configuration shown in FIG. 58 where fluid is permitted to flow from the reservoir of the fill-vial toward the umbrella check valve 377.

Following the mating of the additive sub-system 458 with the dispenser unit, the carriage lock 380, which is carried within a slot 460s formed in end wall 460b of housing 460, is manipulated in the manner previously described to release carriage 346. More particularly, end wall 460b is provided with an opening 481 that is adapted to receive the hook-like locking protuberance 482 that is connected to and extends outwardly from base wall 348a of the carriage assembly 346. Accordingly, when the carriage lock 380 is manipulated in the manner previously described the hook-like protuberance will be released in the manner shown in FIG. 58.

Release of the hook-like protuberance 482 will permit the coiled spring 386 to urge the carriage assembly 346 forwardly of housing from the position shown in FIG. 56 the position shown in FIG. 58. Forward movement of the carriage will be guided by the plurality of spaced-apart guide members 390 that are mounted within the housing and are received within the circumferentially spaced slots 349a formed in carriage base 348a. As the carriage moves forwardly the sidewall of the fluid containing vial assembly 462 will collapse in the manner shown in FIG. 58 of the drawings causing the fluid contained within vial reservoir 461 to be urged outwardly thereof via fluid passageway 476 (FIG. 55) and in the direction of the umbrella valve 377. As before, the ullage 477 functions to ensure that substantially all of the fluid contained within reservoir 461 will be expelled therefrom.

The fluid flowing from vial reservoir 461 will flow past main check valve 368 and around and about the umbrella check valve 377. The fluid will then flow into fluid passageway 330 that is formed in dispenser housing portion 282 via a stub passageway 394a.

From passageway 330, the fluid will flow into inlet passageway 328 and then into reservoir 493 of the container 492 via the central passageway 303a of penetrating member 303. During the adding process, any gases trapped within the flow passageways of the device are vented to atmosphere via a vent "V-1" formed in connector housing portion 285b of control portion 285. Following the completion of the adding process as described in the preceding paragraphs, wherein the fluid medicament "F-1" contained within vial reservoir 461 is added to the reservoir 295, the operating means is used in the manner previously described to control the flow of the fluid mixture from the collapsible reservoir 295 toward the rate control means and then onward toward the administration set.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

The invention claimed is:

1. An apparatus for dispensing medicaments to a patient comprising:
   (a) A fluid dispensing unit comprising:
      (i) a dispenser housing, including a connector portion;
      (ii) a reservoir-defining assembly formed in accordance with an aseptic blow-fill-seal manufacturing technique and comprising a collapsible container having a collapsible fluid reservoir carried by said dispenser housing, said collapsible container having an outlet port and including a top wall, a bottom wall, and a side wall interconnecting said top and bottom walls, said collapsible container further including a neck portion connected to said top wall, said neck portion being sealed by a closure wall;
      (iii) dispenser stored energy means carried by said dispenser housing and operably associated with said collapsible reservoir for collapsing said collapsible reservoir to expel fluid from said outlet port of said collapsible reservoir;
      (iv) dispensing means connected to said outlet port of said collapsible reservoir for dispensing fluid to the patient; and
      (v) fluid flow control means carried by said dispenser housing for controlling fluid flow from said collapsible reservoir toward said dispensing means, said flow control means comprising:
         a. rate control means carried by said dispenser housing for controlling the rate of fluid flow from said collapsible reservoir toward said dispensing means, said rate control means comprising rate control plate having a plurality of fluid flow channels interconnected with said outlet of said collapsible reservoir; and
         b. operating means carried by said dispenser housing for controlling fluid flow between said collapsible reservoir of said fluid dispensing unit and said rate control means, said operating means comprising a penetrating member having a fluid flow passageway and a control knob rotatably carried by said dispenser housing for causing said penetrating means to penetrate said closure wall of said collapsible container; and
   (b) an additive sub-system removably connected to said fluid dispensing unit for adding fluid to said collapsible fluid reservoir of said fluid dispensing unit, said additive sub-system comprising:
      (i) a connector housing removably connected to said connector portion of said dispenser housing of said fluid dispensing unit; and
      (ii) a vial assembly removably receivable within said connector housing, said vial assembly comprising a blow-molded, collapsible fill vial having a closure wall and a collapsible sidewall defining a fluid chamber containing a medicament, said fluid chamber having an outlet port.

2. The apparatus as defined in claim 1 in which said additive sub-system further comprises a stored energy means carried by said connector housing and operably associated with said vial for collapsing said collapsible sidewall, thereof, to expel fluid from said outlet port of said fluid chamber.

3. The apparatus as defined in claim 1 in which said dispenser stored energy means comprises a spring operably interconnected with said collapsible reservoir.

4. The apparatus as defined in claim 1 in which said collapsible sidewall of said vial comprises a bellows structure.

5. The dispensing apparatus as defined in claim 1 in which said collapsible sidewall of said vial comprises a telescoping side wall.

6. The apparatus as defined in claim 1 in which said collapsible fluid reservoir of said fluid dispensing unit comprises a bellows structure.

7. The apparatus as defined in claim 1 in which said dispensing means comprises an administration set, including an administration line interconnected with said outlet of said collapsible reservoir of said fluid dispensing unit.

8. The apparatus as defined in claim 1, in which said fluid dispensing unit further includes a carriage assembly interconnected with said dispenser housing for movement between a first position and a second position, said collapsible fluid reservoir of said fluid dispensing unit being carried by said carriage assembly.

9. The apparatus as defined in claim 1 in which said vial of said vial assembly of said additive sub-system contains a diluent.

10. An apparatus for dispensing medicaments to a patient comprising:
 (a) A fluid dispensing unit comprising:
  (i) a supporting structure, including a connector portion;
  (ii) a carriage assembly carried by said supporting structure for movement between a first position and a second position;
  (iii) a reservoir-defining assembly formed in accordance with an aseptic blow-fill-seal manufacturing technique and comprising a hermetically sealed, collapsible container carried by said carriage, said collapsible container having a fluid reservoir for containing the fluid to be delivered to the patient, said fluid reservoir having an outlet port, said collapsible container including a top wall, a bottom wall, and a collapsible side wall interconnecting said top and bottom walls, said collapsible container further including a neck portion connected to said top wall, said neck portion being sealed by a closure wall;
  (iv) a dispenser stored energy means operably associated with said carriage assembly for movement of said carriage assembly between said first position and second positions;
  (v) an administration set, including an administration line interconnected with said outlet port of said collapsible reservoir; and
  (vi) fluid flow control means carried by said supporting structure for controlling fluid flow from said collapsible reservoir toward said administration set, said flow control means comprising:
   a. rate control means carried by said supporting structure for controlling the rate of fluid flow from said collapsible reservoir toward said administration set, said rate control means comprising rate control plate having a plurality of fluid flow channels interconnected with said outlet of said collapsible reservoir; and
   b. operating means carried by said supporting structure for controlling fluid flow between said collapsible reservoir of said fluid dispensing unit and said rate control means, said operating means comprising a penetrating member having a fluid flow passageway and a control knob rotatably carried by said supporting structure for causing said penetrating means to penetrate said closure wall: and
 (b) an additive sub-system removably connected to said fluid dispensing unit for adding fluid to said collapsible fluid reservoir of said fluid dispensing unit, said additive sub-system comprising:
  (i) a connector housing removably connected to said connector portion of said dispenser housing of said fluid dispensing unit; and
  (ii) a vial assembly removably receivable within said connector housing, said vial assembly comprising a blow-molded, collapsible fill vial having a closure wall and a collapsible sidewall defining a fluid chamber containing a medicament, said fluid chamber having an outlet port.

11. The apparatus as defined in claim 10 in which said collapsible sidewall of said vial comprises a bellows structure.

12. The dispensing apparatus as defined in claim 10 in which said collapsible sidewall of said vial comprises a telescoping side wall.

13. The apparatus as defined in claim 10, in which said vial assembly further comprises a check valve for controlling fluid flow between said outlet port of said fluid chamber and said collapsible fluid reservoir of said fluid dispensing unit.

14. The apparatus as defined in claim 10, in which said vial assembly further comprises a carriage assembly moveable between a first position and a second position, said vial being carried by said carriage assembly.

* * * * *